(12) United States Patent  (10) Patent No.: US 8,221,494 B2
Schreck et al.  (45) Date of Patent: Jul. 17, 2012

(54) APPARATUS AND METHOD OF PLACEMENT OF A GRAFT OR GRAFT SYSTEM

(75) Inventors: Stefan G. Schreck, Fallbrook, CA (US); Joshua Benjamin, Aliso Viejo, CA (US); Kevin Mayberry, Mission Viejo, CA (US)

(73) Assignee: Endologix, Inc., Irvine, CA (US)

( * ) Notice: Subject to any disclaimer, the term of this patent is extended or adjusted under 35 U.S.C. 154(b) by 31 days.

(21) Appl. No.: 12/390,346

(22) Filed: Feb. 20, 2009

(65) Prior Publication Data

US 2009/0216315 A1  Aug. 27, 2009

Related U.S. Application Data

(60) Provisional application No. 61/030,913, filed on Feb. 22, 2008.

(51) Int. Cl.
*A61F 2/82* (2006.01)
(52) U.S. Cl. ......................... 623/1.35; 623/1.13; 623/1.1
(58) Field of Classification Search .................. 623/1.35, 623/1.16, 1.13
See application file for complete search history.

(56) References Cited

U.S. PATENT DOCUMENTS

| | | |
|---|---|---|
| 4,562,596 A | 1/1986 | Kornberg |
| 4,617,932 A | 10/1986 | Kornberg |
| 4,795,465 A | 1/1989 | Marten |
| 5,151,105 A | 9/1992 | Kwan-Gett |
| 5,178,634 A | 1/1993 | Ramos Martinez |
| 5,425,765 A | 6/1995 | Tiefenbrun et al. |
| 5,443,477 A | 8/1995 | Marin et al. |
| 5,464,449 A | 11/1995 | Ryan et al. |
| 5,578,071 A | 11/1996 | Parodi |
| 5,591,195 A | 1/1997 | Taheri et al. |
| 5,628,786 A | 5/1997 | Banas et al. |
| 5,643,171 A | 7/1997 | Bradshaw et al. |
| 5,643,278 A | 7/1997 | Wijay |

(Continued)

FOREIGN PATENT DOCUMENTS

EP   458 568 A1   5/1991

(Continued)

OTHER PUBLICATIONS

U.S. Appl. No. 12/769,506, filed Apr. 28, 2010, Mayberry et al.

(Continued)

*Primary Examiner* — Thomas J Sweet
*Assistant Examiner* — Jason-Dennis Stewart
(74) *Attorney, Agent, or Firm* — Knobbe, Martens, Olson & Bear LLP

(57) ABSTRACT

An endoluminal prosthesis system deployable in a region of a patient's vasculature having one or more branch vessels, having a first main graft body having at least a first and second opening therein and a second main graft body having at least a first and a second opening therein. The first openings can be smaller than the second openings. The second main graft body can be expandable substantially within the first main graft body such that the second openings of each graft body do not substantially cover the first openings of the other graft body. The resulting graft system can have two openings therein, each being defined by the first openings in each of the first and second main graft bodies. One or more branch grafts can be attached to cover the openings in the main graft bodies, and the main graft bodies can have one or more cutouts therein.

24 Claims, 28 Drawing Sheets

U.S. PATENT DOCUMENTS

| | | | |
|---|---|---|---|
| 5,649,952 | A | 7/1997 | Lam |
| 5,651,174 | A | 7/1997 | Schwartz et al. |
| 5,662,580 | A | 9/1997 | Bradshaw et al. |
| 5,662,701 | A | 9/1997 | Plaia et al. |
| 5,669,924 | A | 9/1997 | Shaknovich |
| 5,669,934 | A | 9/1997 | Sawyer |
| 5,676,685 | A | 10/1997 | Razavi |
| 5,681,345 | A | 10/1997 | Euteneuer |
| 5,681,346 | A | 10/1997 | Orth et al. |
| 5,683,449 | A | 11/1997 | Marcade |
| 5,690,642 | A | 11/1997 | Osborne et al. |
| 5,690,643 | A | 11/1997 | Wijay |
| 5,697,971 | A | 12/1997 | Fischell et al. |
| 5,713,917 | A | 2/1998 | Leonhardt et al. |
| 5,720,735 | A | 2/1998 | Dorros |
| 5,755,735 | A | 5/1998 | Richter et al. |
| 5,824,040 | A | 10/1998 | Cox et al. |
| 5,843,162 | A | 12/1998 | Inoue |
| 5,855,600 | A | 1/1999 | Alt |
| 5,928,248 | A | 7/1999 | Acker |
| 5,961,548 | A | 10/1999 | Shmulewitz |
| 5,984,955 | A | 11/1999 | Wisselink |
| 6,033,434 | A | 3/2000 | Borghi |
| 6,059,824 | A | 5/2000 | Taheri |
| 6,068,654 | A | 5/2000 | Berg et al. |
| 6,077,296 | A | 6/2000 | Shokoohi et al. |
| 6,090,128 | A | 7/2000 | Douglas |
| 6,136,006 | A | 10/2000 | Johnson et al. |
| 6,149,681 | A | 11/2000 | Houser et al. |
| 6,156,063 | A | 12/2000 | Douglas |
| 6,165,195 | A | 12/2000 | Wilson et al. |
| 6,165,214 | A | 12/2000 | Lazarus |
| 6,187,033 | B1 | 2/2001 | Schmitt et al. |
| 6,187,036 | B1 | 2/2001 | Shaolian et al. |
| 6,193,745 | B1 * | 2/2001 | Fogarty et al. ............... 623/1.12 |
| 6,197,049 | B1 | 3/2001 | Shaolian et al. |
| 6,210,429 | B1 | 4/2001 | Vardi et al. |
| 6,221,090 | B1 | 4/2001 | Wilson |
| 6,221,098 | B1 | 4/2001 | Wilson |
| 6,224,609 | B1 | 5/2001 | Ressemann et al. |
| 6,235,051 | B1 | 5/2001 | Murphy |
| 6,261,316 | B1 | 7/2001 | Shaolian et al. |
| 6,264,682 | B1 | 7/2001 | Wilson et al. |
| 6,280,466 | B1 | 8/2001 | Kugler et al. |
| 6,283,991 | B1 | 9/2001 | Cox et al. |
| 6,325,826 | B1 | 12/2001 | Vardi et al. |
| 6,331,190 | B1 | 12/2001 | Shokoohi et al. |
| 6,334,867 | B1 | 1/2002 | Anson |
| 6,348,066 | B1 | 2/2002 | Pinchuk et al. |
| 6,350,278 | B1 | 2/2002 | Lenker et al. |
| 6,352,553 | B1 | 3/2002 | Van der Burg et al. |
| 6,352,561 | B1 | 3/2002 | Leopold et al. |
| 6,355,060 | B1 | 3/2002 | Lenker et al. |
| 6,361,544 | B1 | 3/2002 | Wilson et al. |
| 6,361,555 | B1 | 3/2002 | Wilson |
| 6,361,557 | B1 | 3/2002 | Gittings et al. |
| 6,361,637 | B2 | 3/2002 | Martin et al. |
| 6,383,213 | B2 | 5/2002 | Wilson et al. |
| 6,387,120 | B2 | 5/2002 | Wilson et al. |
| 6,395,018 | B1 | 5/2002 | Castaneda |
| 6,398,807 | B1 | 6/2002 | Chouinard et al. |
| 6,409,750 | B1 | 6/2002 | Hyodoh et al. |
| 6,409,757 | B1 | 6/2002 | Trout, III et al. |
| 6,416,474 | B1 | 7/2002 | Penner et al. |
| 6,416,542 | B1 | 7/2002 | Marcade et al. |
| 6,428,565 | B1 | 8/2002 | Wisselink |
| 6,428,567 | B2 | 8/2002 | Wilson et al. |
| 6,432,131 | B1 | 8/2002 | Ravenscroft |
| 6,458,152 | B1 | 10/2002 | Khosravi et al. |
| 6,464,721 | B1 | 10/2002 | Marcade et al. |
| 6,475,170 | B1 | 11/2002 | Doron et al. |
| 6,491,719 | B1 | 12/2002 | Fogarty et al. |
| 6,500,182 | B2 | 12/2002 | Foster |
| 6,500,202 | B1 | 12/2002 | Shaolian et al. |
| 6,508,833 | B2 | 1/2003 | Pavcnik et al. |
| 6,508,835 | B1 | 1/2003 | Schaolian et al. |
| 6,508,836 | B2 | 1/2003 | Wilson et al. |
| 6,511,325 | B1 | 1/2003 | Lalka et al. |
| 6,514,281 | B1 | 2/2003 | Blaeser et al. |
| 6,517,572 | B2 | 2/2003 | Kugler et al. |
| 6,517,573 | B1 | 2/2003 | Pollock et al. |
| 6,524,335 | B1 | 2/2003 | Hartley et al. |
| 6,533,811 | B1 | 3/2003 | Ryan et al. |
| 6,558,396 | B1 | 5/2003 | Inoue |
| 6,565,596 | B1 | 5/2003 | White et al. |
| 6,565,597 | B1 | 5/2003 | Fearnot et al. |
| RE38,146 | E | 6/2003 | Palmaz et al. |
| 6,572,645 | B2 | 6/2003 | Leonhardt |
| 6,579,312 | B2 | 6/2003 | Wilson et al. |
| 6,582,394 | B1 | 6/2003 | Reiss et al. |
| 6,585,758 | B1 | 7/2003 | Chouinard et al. |
| 6,592,614 | B2 | 7/2003 | Lenker et al. |
| 6,592,615 | B1 | 7/2003 | Marcade et al. |
| 6,599,315 | B2 | 7/2003 | Wilson |
| 6,613,073 | B1 | 9/2003 | White et al. |
| 6,645,242 | B1 | 11/2003 | Quinn |
| 6,652,567 | B1 | 11/2003 | Deaton |
| 6,660,033 | B1 | 12/2003 | Marcade et al. |
| 6,669,718 | B2 | 12/2003 | Besselink |
| 6,692,483 | B2 | 2/2004 | Vardi et al. |
| 6,706,062 | B2 | 3/2004 | Vardi et al. |
| 6,723,116 | B2 | 4/2004 | Taheri |
| 6,761,733 | B2 | 7/2004 | Chobotov et al. |
| 6,767,359 | B2 | 7/2004 | Weadcock |
| 6,793,671 | B2 | 9/2004 | Wall |
| 6,802,859 | B1 | 10/2004 | Pazienza et al. |
| 6,811,566 | B1 | 11/2004 | Penn et al. |
| 6,814,752 | B1 | 11/2004 | Chuter |
| 6,827,726 | B2 | 12/2004 | Parodi |
| 6,835,203 | B1 | 12/2004 | Vardi et al. |
| 6,875,229 | B2 | 4/2005 | Wilson et al. |
| 6,896,699 | B2 | 5/2005 | Wilson et al. |
| 6,908,477 | B2 | 6/2005 | McGuckin, Jr. et al. |
| 6,918,925 | B2 | 7/2005 | Tehrani |
| 6,936,065 | B2 | 8/2005 | Khan et al. |
| 6,939,371 | B2 | 9/2005 | Kugler et al. |
| 6,955,688 | B2 | 10/2005 | Wilson et al. |
| 6,960,217 | B2 | 11/2005 | Bolduc |
| 6,962,602 | B2 | 11/2005 | Vardi et al. |
| 6,974,471 | B2 | 12/2005 | Van Schie et al. |
| 6,989,026 | B2 | 1/2006 | Richter et al. |
| 7,014,653 | B2 | 3/2006 | Ouriel et al. |
| 7,029,496 | B2 | 4/2006 | Rakos et al. |
| 7,074,235 | B1 | 7/2006 | Roy |
| 7,105,015 | B2 | 9/2006 | Goshgarian |
| 7,118,593 | B2 | 10/2006 | Davidson et al. |
| 7,131,991 | B2 | 11/2006 | Zarins et al. |
| 7,175,651 | B2 | 2/2007 | Kerr |
| 7,189,257 | B2 | 3/2007 | Schmitt et al. |
| 7,220,275 | B2 | 5/2007 | Davidson et al. |
| 7,229,472 | B2 | 6/2007 | DePalma et al. |
| 7,232,449 | B2 | 6/2007 | Sharkawy et al. |
| 7,235,095 | B2 | 6/2007 | Haverkost et al. |
| 7,241,300 | B2 | 7/2007 | Sharkawy et al. |
| 7,294,145 | B2 | 11/2007 | Ward |
| 7,300,460 | B2 | 11/2007 | Levine et al. |
| 7,306,623 | B2 | 12/2007 | Watson |
| 7,314,483 | B2 | 1/2008 | Landau et al. |
| 7,341,598 | B2 | 3/2008 | Davidson et al. |
| 7,407,509 | B2 | 8/2008 | Greenberg et al. |
| 7,413,573 | B2 | 8/2008 | Hartley et al. |
| 7,425,219 | B2 | 9/2008 | Quadri |
| 7,438,721 | B2 | 10/2008 | Doig et al. |
| 7,491,230 | B2 | 2/2009 | Holman et al. |
| 7,520,895 | B2 | 4/2009 | Douglas et al. |
| 7,537,606 | B2 | 5/2009 | Hartley et al. |
| 7,582,111 | B2 | 9/2009 | Krolik et al. |
| 7,591,843 | B1 | 9/2009 | Escano et al. |
| 7,615,072 | B2 | 11/2009 | Rust et al. |
| 2001/0014823 | A1 | 8/2001 | Ressemann |
| 2001/0027338 | A1 | 10/2001 | Greenberg |
| 2001/0037142 | A1 | 11/2001 | Stelter et al. |
| 2002/0049412 | A1 | 4/2002 | Madrid et al. |
| 2002/0138088 | A1 | 9/2002 | Nash et al. |
| 2002/0143383 | A1 | 10/2002 | Parodi |
| 2002/0147491 | A1 | 10/2002 | Khan et al. |
| 2002/0156516 | A1 | 10/2002 | Vardi et al. |

| | | |
|---|---|---|
| 2002/0193872 A1 | 12/2002 | Trout et al. |
| 2003/0004560 A1 | 1/2003 | Chobotov et al. |
| 2003/0083678 A1 | 5/2003 | Herweck et al. |
| 2004/0049257 A1* | 3/2004 | Kaspersen et al. ............ 623/1.13 |
| 2004/0073288 A1 | 4/2004 | Kerr |
| 2004/0093058 A1 | 5/2004 | Cottone et al. |
| 2004/0106972 A1 | 6/2004 | Deaton |
| 2004/0127975 A1 | 7/2004 | Levine et al. |
| 2004/0193254 A1 | 9/2004 | Greenberg et al. |
| 2004/0215327 A1 | 10/2004 | Doig et al. |
| 2004/0230287 A1 | 11/2004 | Hartley et al. |
| 2004/0236403 A1 | 11/2004 | Leonhardt et al. |
| 2005/0015135 A1 | 1/2005 | Shanley |
| 2005/0033405 A1 | 2/2005 | Solovay |
| 2005/0059923 A1 | 3/2005 | Gamboa |
| 2005/0060026 A1 | 3/2005 | Gamboa |
| 2005/0131517 A1 | 6/2005 | Hartley et al. |
| 2005/0131518 A1 | 6/2005 | Hartley et al. |
| 2005/0131526 A1 | 6/2005 | Wong |
| 2005/0149166 A1 | 7/2005 | Schaeffer et al. |
| 2005/0165470 A1 | 7/2005 | Weber |
| 2005/0171597 A1 | 8/2005 | Boatman et al. |
| 2005/0171598 A1 | 8/2005 | Schaeffer |
| 2005/0177221 A1 | 8/2005 | Mustapha |
| 2005/0215327 A1 | 9/2005 | Weisel et al. |
| 2005/0222668 A1 | 10/2005 | Schaeffer et al. |
| 2006/0036315 A1 | 2/2006 | Yadin et al. |
| 2006/0058864 A1 | 3/2006 | Schaeffer et al. |
| 2006/0074475 A1 | 4/2006 | Gumm |
| 2006/0089704 A1 | 4/2006 | Douglas |
| 2006/0149350 A1 | 7/2006 | Patel et al. |
| 2006/0155358 A1 | 7/2006 | LaDuca et al. |
| 2006/0155363 A1 | 7/2006 | LaDuca et al. |
| 2006/0155366 A1 | 7/2006 | LaDuca et al. |
| 2006/0224232 A1 | 10/2006 | Chobotov |
| 2006/0229669 A1 | 10/2006 | Mirizzi et al. |
| 2006/0247761 A1 | 11/2006 | Greenberg et al. |
| 2006/0271164 A1 | 11/2006 | Shaolian et al. |
| 2007/0016280 A1 | 1/2007 | Yacoby et al. |
| 2007/0021828 A1 | 1/2007 | Krolik et al. |
| 2007/0043425 A1 | 2/2007 | Hartley et al. |
| 2007/0050016 A1 | 3/2007 | Gregorich et al. |
| 2007/0055350 A1 | 3/2007 | Erickson |
| 2007/0055360 A1 | 3/2007 | Hanson et al. |
| 2007/0055362 A1 | 3/2007 | Brown |
| 2007/0067019 A1 | 3/2007 | Miller et al. |
| 2007/0067023 A1 | 3/2007 | Kveen et al. |
| 2007/0073376 A1 | 3/2007 | Krolik et al. |
| 2007/0073388 A1 | 3/2007 | Krolik et al. |
| 2007/0142896 A1 | 6/2007 | Anderson et al. |
| 2007/0150051 A1 | 6/2007 | Arnault De La Menardiere et al. |
| 2007/0167955 A1 | 7/2007 | Arnault De La Menardiere et al. |
| 2007/0168019 A1 | 7/2007 | Amplatz et al. |
| 2007/0173921 A1 | 7/2007 | Wholey et al. |
| 2007/0179592 A1 | 8/2007 | Schaeffer |
| 2007/0219620 A1 | 9/2007 | Eells et al. |
| 2007/0219621 A1 | 9/2007 | Hartley et al. |
| 2007/0225796 A1 | 9/2007 | Yadin et al. |
| 2007/0225797 A1* | 9/2007 | Krivoruhko ................. 623/1.35 |
| 2007/0225798 A1 | 9/2007 | Gregorich |
| 2007/0244542 A1 | 10/2007 | Greenan et al. |
| 2007/0244547 A1* | 10/2007 | Greenan ..................... 623/1.35 |
| 2007/0248640 A1 | 10/2007 | Karabey et al. |
| 2007/0260304 A1 | 11/2007 | Gregorich et al. |
| 2007/0293940 A1 | 12/2007 | Schaeffer et al. |
| 2007/0299494 A1 | 12/2007 | Zukowski |
| 2007/0299495 A1 | 12/2007 | Zukowski et al. |
| 2007/0299497 A1 | 12/2007 | Shaolian et al. |
| 2007/0299499 A1 | 12/2007 | Hartley et al. |
| 2008/0009932 A1 | 1/2008 | Ta et al. |
| 2008/0009933 A1 | 1/2008 | Ta et al. |
| 2008/0015681 A1 | 1/2008 | Wilson et al. |
| 2008/0033525 A1 | 2/2008 | Shaked et al. |
| 2008/0058918 A1 | 3/2008 | Watson |
| 2008/0065197 A1 | 3/2008 | Meyer et al. |
| 2008/0071343 A1 | 3/2008 | Mayberry et al. |
| 2008/0086191 A1 | 4/2008 | Valencia et al. |
| 2008/0109065 A1 | 5/2008 | Bowe |
| 2008/0114444 A1* | 5/2008 | Yu ................................ 623/1.13 |
| 2008/0114446 A1 | 5/2008 | Hartley |
| 2008/0133000 A1 | 6/2008 | Molony |
| 2008/0167704 A1 | 7/2008 | Wright et al. |
| 2008/0172119 A1 | 7/2008 | Yamasaki et al. |
| 2008/0172122 A1 | 7/2008 | Mayberry et al. |
| 2008/0188921 A1 | 8/2008 | Yamasaki et al. |
| 2008/0208319 A1 | 8/2008 | Rabkin et al. |
| 2008/0262595 A1* | 10/2008 | Chu et al. ..................... 623/1.13 |
| 2008/0262596 A1 | 10/2008 | Xiao |
| 2008/0269866 A1 | 10/2008 | Hamer et al. |
| 2008/0269867 A1 | 10/2008 | Johnson |
| 2008/0275542 A1 | 11/2008 | LaDuca |
| 2008/0281399 A1 | 11/2008 | Hartley |
| 2008/0288044 A1 | 11/2008 | Osborne et al. |
| 2009/0005847 A1 | 1/2009 | Adams |
| 2009/0012602 A1 | 1/2009 | Quadri |
| 2009/0043373 A1 | 2/2009 | Arnault De la Menardiere et al. |
| 2009/0043377 A1 | 2/2009 | Greenberg et al. |
| 2009/0069880 A1 | 3/2009 | Vonderwalde et al. |
| 2009/0109065 A1 | 4/2009 | Pinheiro |
| 2009/0254170 A1 | 10/2009 | Hartley et al. |
| 2009/0259290 A1 | 10/2009 | Bruszewski et al. |
| 2009/0259296 A1 | 10/2009 | Mclff et al. |
| 2009/0259298 A1 | 10/2009 | Mayberry et al. |
| 2009/0264985 A1 | 10/2009 | Bruszewski |
| 2009/0287145 A1 | 11/2009 | Cragg et al. |
| 2010/0063576 A1 | 3/2010 | Schaeffer et al. |

FOREIGN PATENT DOCUMENTS

| | | |
|---|---|---|
| EP | 177 330 B1 | 6/1991 |
| EP | 282 175 B1 | 11/1991 |
| EP | 323 176 B1 | 3/1994 |
| EP | 621 015 A1 | 10/1994 |
| EP | 782 841 A2 | 2/1995 |
| EP | 783 873 A2 | 2/1995 |
| EP | 783 874 A2 | 2/1995 |
| EP | 689 806 A2 | 1/1996 |
| EP | 712 614 A1 | 5/1996 |
| EP | 732 088 A3 | 9/1996 |
| EP | 747 020 A2 | 12/1996 |
| EP | 732 089 A3 | 2/1997 |
| EP | 775 470 A1 | 5/1997 |
| EP | 880 948 A1 | 5/1998 |
| EP | 880 938 A1 | 12/1998 |
| EP | 904 745 A2 | 3/1999 |
| EP | 732 088 B1 | 4/2000 |
| EP | 1470797 | 10/2004 |
| ES | 1 038 606 | 7/1998 |
| WO | WO 2006028925 | 3/2006 |

OTHER PUBLICATIONS

International Search Report and Written Opinion of the International Searching Authority, dated Apr. 13, 2009, re PCT/US200934755 in 11 pages.

* cited by examiner

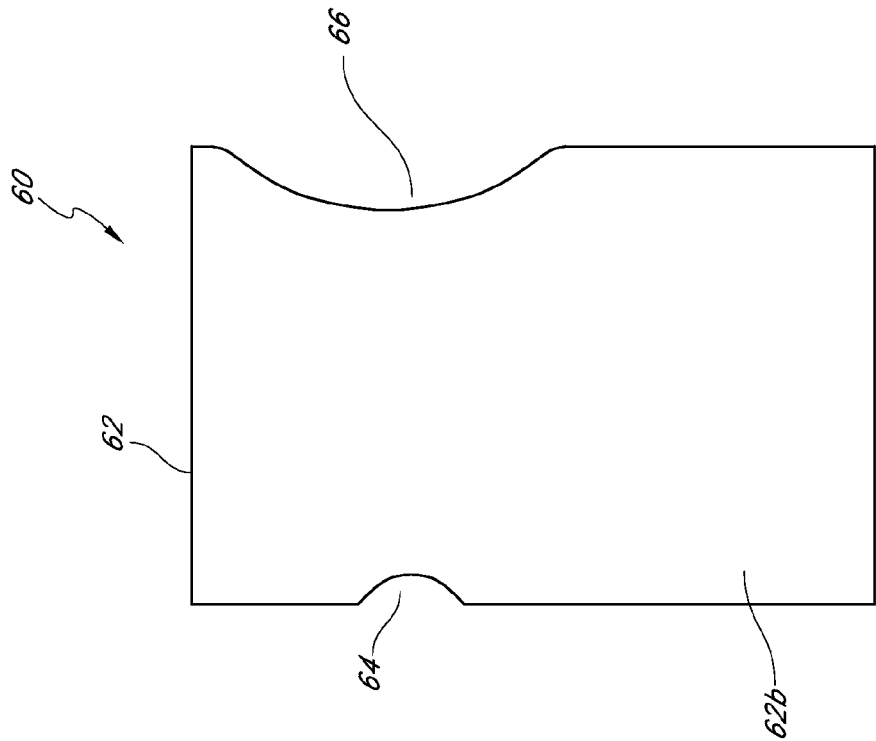
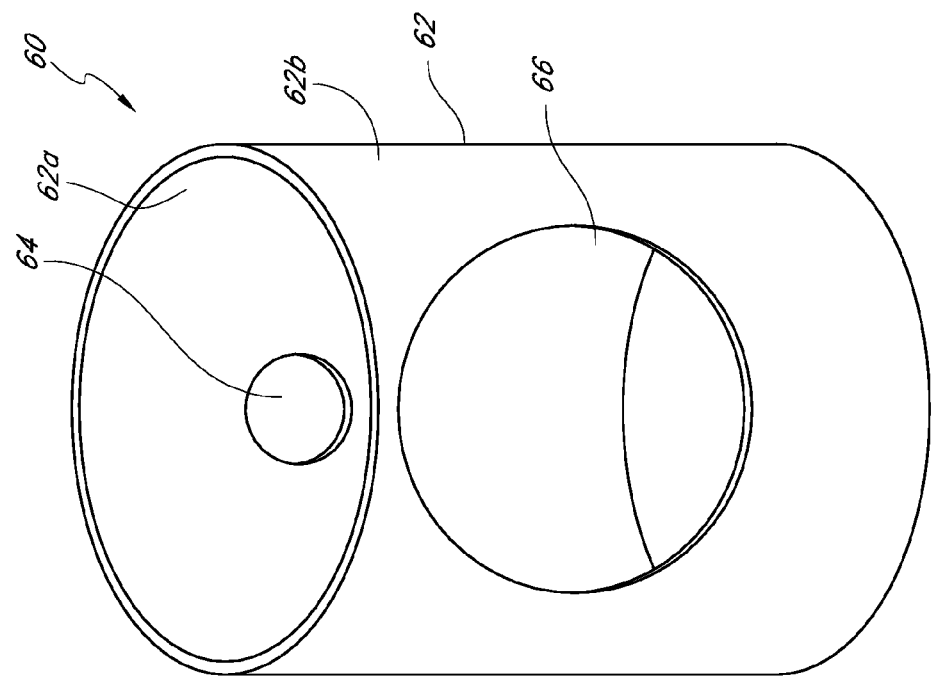
FIG. 10B
FIG. 10A

APPARATUS AND METHOD OF PLACEMENT OF A GRAFT OR GRAFT SYSTEM

PRIORITY CLAIM AND INCORPORATION BY REFERENCE

This application claims the benefit under 35 U.S.C. §119 of U.S. Provisional Patent Application No. 61/030,913, filed Feb. 22, 2008 (entitled "METHOD OF PLACEMENT OF AN AORTIC GRAFT"), the entirety of which is hereby incorporated by reference as if fully set forth herein.

BACKGROUND

1. Technical Field

The present invention relates to endoluminal vascular prostheses and methods of placing such prostheses, and, in one application, to endoluminal vascular prostheses for use in the treatment of vessels with branches.

2. Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of polyester, urethane, Dacron®, Teflon®, or other suitable material.

To perform the surgical procedure requires exposure of the aorta through an abdominal incision which can extend from the rib cage to the pubis. The aorta must typically be closed both above and below the aneurysm, so that the aneurysm can then be opened and the thrombus, or blood clot, and arteriosclerotic debris removed. Small arterial branches from the back wall of the aorta are tied off. The Dacron® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. Since the graft must typically be secured, or sutured, to the remaining portion of the aorta, it is many times difficult to perform the suturing step because the thrombosis present on the remaining portion of the aorta, and that remaining portion of the aorta wall may many times be friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft in the endoluminal position (within the lumen of the artery). By this method, the graft is attached to the internal surface of an arterial wall by means of attachment devices (expandable stents), typically one above the aneurysm and a second stent below the aneurysm.

Stents can permit fixation of a graft to the internal surface of an arterial wall without sewing or an open surgical procedure. Expansion of radially expandable stents is conventionally accomplished by dilating a balloon at the distal end of a balloon catheter. In U.S. Pat. No. 4,776,337, for example, Palmaz describes a balloon-expandable stent for endovascular treatments. Also known are self-expanding stents, such as described in U.S. Pat. No. 4,655,771 to Wallsten.

In certain conditions, the diseased region of the blood vessels extends across branch vessels. The blood flow into these branch vessels is critical for the perfusion of the peripheral regions of the body and vital organs. Many arteries branch off the aorta. For example, the carotid arteries supply blood into the brain, the renal arteries supply blood into the kidneys, the superior mesenteric artery ("SMA") supplies the pancreas, and hypogastric arteries to the reproductive organs, and the subclavian arteries supply blood to the arms. When the aorta is diseased, the branch vessels may also be affected. Thoracic aortic aneurysms may involve the subclavian and carotid arteries, abdominal aneurysms may involve the SMA, renal and hypogastric arteries. Aortic dissections may involve all branch vessels mentioned above.

There is a need to place endoluminal prostheses in the aorta without obstructing critical branch vessels. The embodiments of the endoluminal prostheses disclosed herein provide a solution to the problems described above.

SUMMARY OF SOME EXEMPLIFYING EMBODIMENTS

Some embodiments of the endoluminal prosthesis disclosed herein pertain to the design and method of placement of a branch graft system for endovascular treatment of diseased blood vessels. The branch graft system can comprise a tubular expandable main body and at least one branch graft. The branch graft is made from an expandable material, which can be ePTFE. In some embodiments, the diameter of the branch graft can be sufficiently small to be manipulated into the desired vascular position by moving the branch graft over a guidewire. The branch graft can be expanded to the diameter of the branch vessel by mechanical means, which can be a dilation balloon. In another embodiment of an endoluminal prosthesis, the main body of the branch graft system can have one large opening in the wall of the graft for the treatment of a second branch vessel. A second branch graft system can be placed inside of the first branch graft system, wherein the branch graft of the second branch graft system passed through the opening of the first branch graft system and the large opening of the second branch graft system overlaps with the branch graft of the first branch graft system.

In some embodiments, an endoluminal prosthesis system is disclosed that can comprise a first endoluminal prosthesis comprising a first main graft body having at least a first and a second opening therein and a second endoluminal prosthesis comprising a second main graft body having at least a first and a second opening therein. The first opening in the first main graft body can be smaller than the second opening in the first main graft body, and the first opening in the second main graft body can be smaller than the second opening in the second main graft body. Further, the second main graft body can be configured to be expandable substantially within the first main graft body such that the second opening of the second main graft body does not cover any portion of the first opening in the first main graft body, and such that the second opening of the first main graft body does not cover any portion of the first opening in the second main graft body. In some embodiments, when the second main graft body has been expanded within the first main graft body, the resulting endoluminal prosthesis system can have two small openings therein that are each approximately equivalent in diameter to the first opening in each of the first and second main graft bodies.

In some embodiments, a method of deploying a branch graft system in a portion of a patient's blood vessel having at least a first and a second branch blood vessel is described. In some embodiments, the method can comprise positioning a first main graft body having at least a first and a second opening therein in the patient's blood vessel so that the first opening can be substantially aligned with the first branch blood vessel and so that the second opening can be sufficiently aligned with the second branch blood vessel so that the first main graft body does not substantially cover either the first or second branch blood vessel. The method can further comprise positioning at least a portion of a second main graft body having at least a first and a second opening therein within the inside of the first main graft body so that the first opening of the second main graft body can be substantially aligned with the second branch blood vessel and so that the second opening of the second main graft body can be sufficiently aligned with the first branch blood vessel so that the second main graft body does not substantially cover either the first or second branch blood vessel. The method can further comprise expanding the first and second main graft bodies against the patient's blood vessel to create a multi-layer graft system having two openings through the wall thereof that are substantially aligned with the first and second blood vessels and have a diameter substantially equal to the first opening of each of the first and second main graft bodies, and supporting the first and second main graft bodies against the patient's blood vessel. In some embodiments the second opening in each of the first and second main graft bodies can be substantially larger than the first opening in each of the first and second main graft bodies.

In some embodiments, an endoluminal prosthesis is disclosed that can comprise an expandable main graft portion having an axial opening therethrough and at least a first branch opening therein and an expandable branch graft portion having a proximal end portion, a distal end portion, and an axial opening therethrough. In some embodiments, the branch graft portion can be supported by the main graft portion and the branch graft portion can be supported by the main graft portion so that the proximal end portion of the branch graft portion can be positioned around a periphery of the first branch opening in the main graft, and such that the axial opening through the branch graft portion can be in communication with the first branch opening formed in the main graft portion. In some embodiments, at least the distal end portion of the branch graft portion can be in a first, unexpanded state. In other words, in some embodiments, before the branch graft has been deployed in the desired vascular location, the distal end portion of the branch graft portion can have a diameter that is less than the diameter of the proximal end portion of the branch graft portion.

BRIEF DESCRIPTION OF THE DRAWINGS

FIGS. 10A and 10B are a perspective view and a side view, respectively, of another embodiment of a fenestrated endoluminal prosthesis.

DETAILED DESCRIPTION OF SOME EXEMPLIFYING EMBODIMENTS

The following detailed description is now directed to certain specific embodiments of the disclosure. In this description, reference is made to the drawings wherein like parts are designated with like numerals throughout the description and the drawings.

Certain embodiments described herein are directed to systems, methods, and apparatuses to treat lesions, aneurysms, or other defects in the aorta, including, but not limited to, the thoracic, ascending, and abdominal aorta, to name a few. However, the systems, methods, and apparatuses may have application to other vessels or areas of the body, or to other fields, and such additional applications are intended to form a part of this disclosure. For example, it will be appreciated that the systems, methods, and apparatuses may have application to the treatment of blood vessels in animals. In short, the embodiments and/or aspects of the endoluminal prosthesis systems, methods, and apparatuses described herein can be applied to other parts of the body or may have other applications apart from the treatment of the thoracic, ascending, and abdominal aorta. And, while specific embodiments may be described herein with regard to particular portions of the aorta, it is to be understood that the embodiments described can be adapted for use in other portions of the aorta or other portions of the body and are not limited to the aortic portions described.

Figures 1A, 1B:
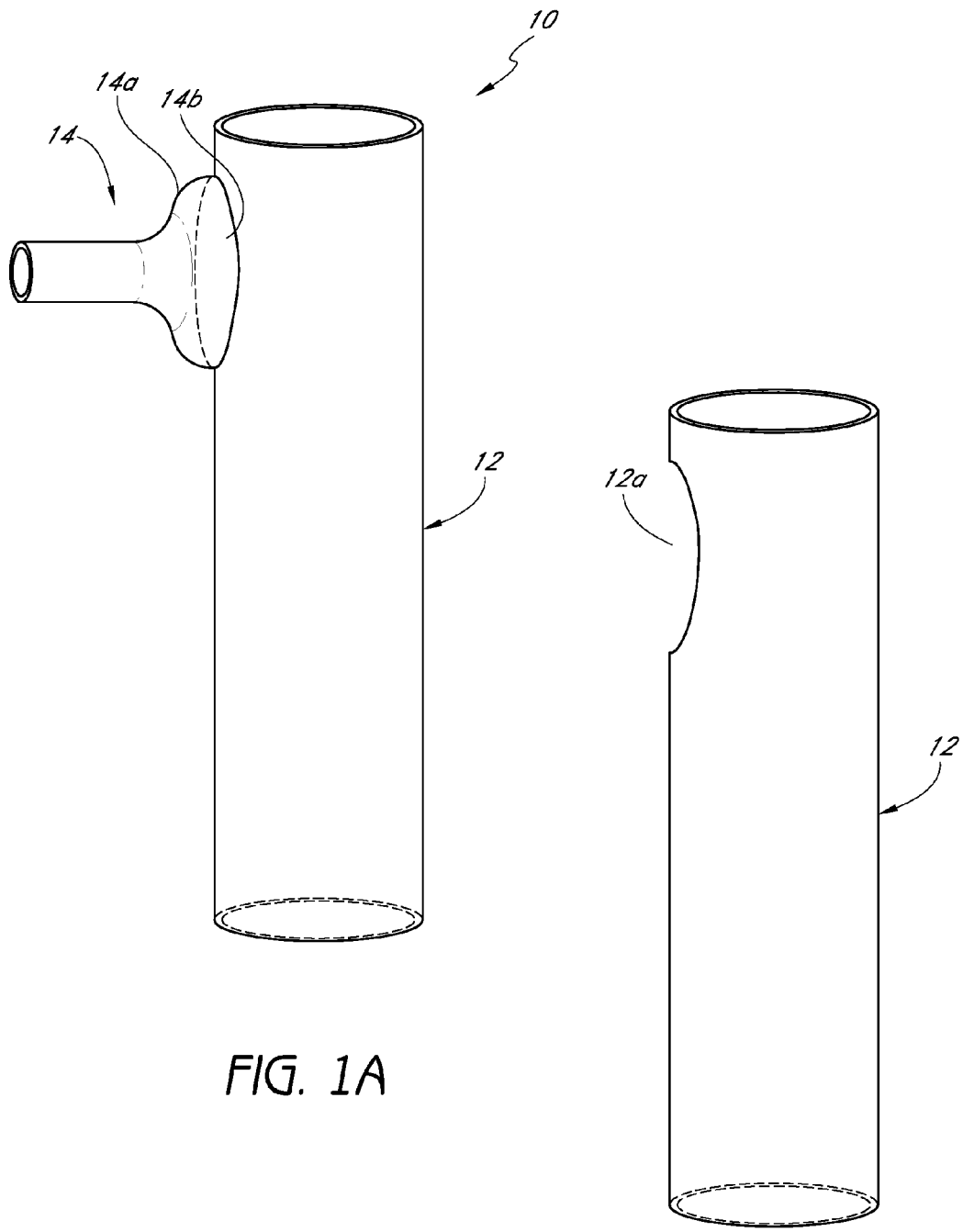
FIG. 1A is a perspective view of an embodiment of an endoluminal prosthesis.
FIG. 1B is a perspective view of the main body graft of the embodiment of the endoluminal prosthesis illustrated in FIG. 1A.

FIG. 1A is a perspective view of an embodiment of an endoluminal prosthesis 10 (also sometimes referred to herein as a branch graft system) having a main body graft 12 and at least one branch graft 14. The branch graft 14 is shown in a partially expanded state. In some configurations, the main body graft 12 can be positioned in the abdominal aorta, which the branch graft or grafts 14 can be positioned within the left or right renal artery. In some configurations, the branch graft or grafts 14 can be positioned within any one or combination of the following: left renal artery, right renal artery, second lumbar, testicular, inferior mesenteric, middle sacral, or other vessels branching from the aorta. Thus, in some embodiments, the endoluminal prosthesis 10 can comprise any number of branch grafts 14 that are required for the specific application, including, but not limited to, two, three, or more branch grafts 14.

Because the branch graft or grafts 14 can be configured to conform to a wide range of vessels and a wide range of positions, the branch graft or grafts 14 can be of any suitable size, shape, or configuration, and can be attached to the main body graft 12 in any of a wide variety of locations. Therefore, some embodiments of the endoluminal prosthesis 10 can comprise only one branch graft 14. However, in some embodiments, the endoluminal prosthesis 10 can comprise two or more branch grafts 14, or any suitable number depending on the application.

Figure 1C:
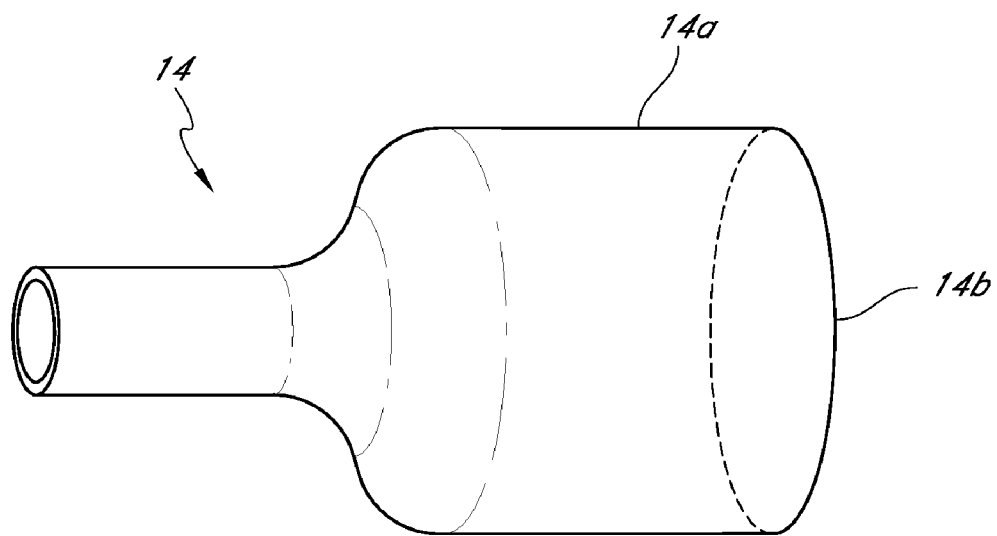
FIG. 1C is a perspective view of the partially expanded branch graft of the embodiment of the endoluminal prosthesis illustrated in FIG. 1A.
Figure 1D:
FIG. 1D is a perspective view of the branch graft illustrated in FIG. 1B before the branch graft 14 has been partially expanded.
Figure 1E:
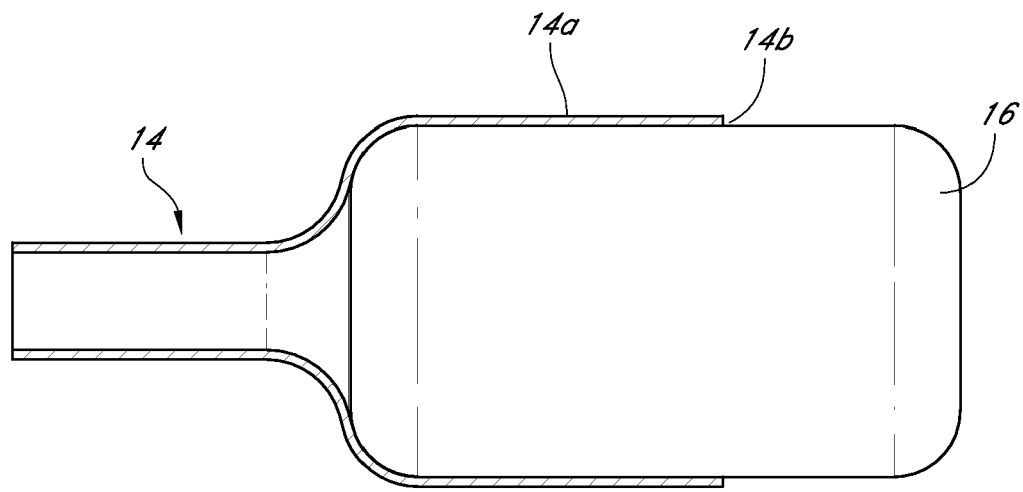
FIG. 1E is a partial section view of the branch graft illustrated in FIG. 1D, wherein a portion of the branch graft has been partially expanded with the use of the balloon expander.

FIG. 1B is a perspective view of the main body graft 12 of the embodiment of the endoluminal prosthesis 10 illustrated in FIG. 1A. FIG. 1C is a perspective view of the partially expanded branch graft 14 of the embodiment of the endoluminal prosthesis 10 illustrated in FIG. 1A. FIG. 1C illustrates the branch graft 14 before it has been assembled with the main body graft 12 to form the embodiment of the endoluminal prosthesis 10 illustrated in FIG. 1A. FIG. 1D is a perspective view of the branch graft 14 illustrated in FIG. 1B before the branch graft 14 has been partially expanded. FIG. 1E is a partial section view of the branch graft illustrated in FIG. 1D, wherein a portion of the branch graft 14 has been partially expanded with the use of the balloon expander 16.

With reference to FIGS. 1A-1E, one of many suitable methods for fabricating some embodiments of the endoluminal prosthesis 10 will be described. As will be described, the branch graft 14 in the pre-expanded state as shown in FIG. 1D can be partially expanded by the balloon expander 16 to form the partially expanded branch graft 14 shown in FIGS. 1A, 1C. In some embodiments, only the proximal end portion 14a of the branch graft 14 (i.e., the end of the branch graft 14 closest to opening 14b) can preferably be expanded by the balloon expander 16. To expand the branch graft 14, the balloon expander 16 can be partially inserted into the proximal end portion 14a of the pre-expanded branch graft 14 (shown in FIG. 1D) and inflated until the proximal end portion 14a of the branch graft 14 reaches the desired or suitable size. While the expansion being of the branch graft 14 can be performed with a balloon expander 16, as is illustrated in FIG. 1E, any suitable method of expanding the branch graft 14 can be employed, including but without limitation other forms of mechanical expanders. Thus, FIG. 1E illustrates only one of several suitable methods for partially expanding the pre-expanded branch graft 14 illustrated in FIG. 1D to form the partially expanded branch graft 14 illustrated in FIG. 1A, 1C.

In some arrangements, the proximal end portion 14a of the branch graft 14 can be expanded to approximately match or conform to the expected diameter of the branch vessel and/or the diameter of the opening 12a. Thus, the branch graft 14 can be configured so as to be expandable over a wide range of sizes and cross-sectional shapes, depending on the size or shape of the branch vessel that the branch graft 14 is intended to be supported by. After removing the balloon expander 16, the proximal portion of the partially expanded branch graft 14 can be trimmed to conform to the opening 12a formed in the main body graft 12. The opening 12a can be sized and positioned to conform to the desired size location of the partially expanded branch graft 14. Thereafter, as mentioned, the branch graft 14 can be attached to the main body graft 12 using adhesive, sutures, or any other suitable attachment method, to form the endoluminal prosthesis 10 illustrated in FIG. 1A. Any portion of the endoluminal prosthesis 10, including the main body graft 12 and/or the branch graft 14, or any other endoluminal prosthesis disclosed herein can be formed from PTFE, ePTFE, polyester, urethane, Dacron, Dacron®, Teflon®, or any other distensible polymeric material or other suitable material.

In some embodiments, the sutures used to attach the branch graft 14 (or any other branch graft disclosed herein) to the main body 12 (or any other main body or graft portion disclosed herein) can be made from a radiopaque ("RO") material so that the location of the branch graft can be perceived in an x-ray or other radiation transmission during deployment. In some embodiments, the sutures can be made from platinum, gold, barium sulfate, or any other suitable RO material. Alternatively, RO markers can be sewn to or otherwise attached to the main body of the endoluminal prosthesis at any suitable position, such as but not limited to adjacent to or on the branch graft or near the end portions of the main body, again to aid in visualization of the endoluminal prosthesis during deployment.

In some embodiments, the diameter of the pre-expanded branch graft 14 (shown in FIG. 1D) can be from approximately 1 mm or less to approximately 3 mm or more. However, the pre-expanded diameter of the pre-expanded branch graft 14 (as illustrated in FIG. 1D) can be any suitable cross-sectional size or shape depending on the size and shape of the target artery or blood vessel. Additionally, in some embodiments, the shape of the pre-expanded branch graft 14 can be cylindrical. However, the shape of the pre-expanded branch graft 14 is not so limited. The pre-expanded branch graft 14 can define a curved, angled, tapered or other suitable shape.

In some embodiments, the branch graft 14 can be integrally formed with the main body graft 12. In some embodiments, the branch graft 14 can be attached to the main body graft 12 using sutures, adhesive, or any other suitable attachment material or method. The junction between the branch graft or grafts 14 and the main body graft 12 can be sealed so as to substantially inhibit or prevent blood from leaking through the junction and flowing between the main body graft 12 and the aorta or other blood vessel that the main body graft 12 is positioned within. In some embodiments, the junction between the branch graft or grafts 14 and the main body graft 12 can be sealed so as to inhibit or prevent at least the majority of the blood flowing therethrough from leaking through the junction and flowing between the main body graft 12 and the aorta or other blood vessel that the main body graft 12 is positioned within. In this configuration, the endoluminal prosthesis 10 can be less susceptible to leakage between the main body graft 12 and the aorta or blood vessel at the blood vessel branch point as compared to conventional fenestrated graft systems.

In some embodiments, the main body graft 12 or the branch graft 14 of the endoluminal prosthesis 10 can be similar in size, material, or other details to other suitable expandable bifurcated or non-bifurcated endoluminal prostheses presently known or later developed in the art, or can be of any size, material, or other details of any other prosthesis presently known or later developed in the art. For example, without limitation, in some embodiments, the main body graft 12 or the branch graft 14 can comprise any of the materials, features, or other aspects of the embodiments of the polymeric sleeves or the tubular wire supports disclosed in U.S. Pat. No. 6,077,296 (titled ENDOLUMINAL VASCULAR PROSTHESIS and filed on Mar. 4, 1998), U.S. Pat. No. 6,187,036 (titled ENDOLUMINAL VASCULAR PROSTHESIS and filed on Dec. 11, 1998), U.S. Pat. No. 6,197,049 (titled ARTICULATING BIFURCATION GRAFT and filed on Feb. 17, 1999), U.S. Pat. No. 6,500,202 (titled BIFURCATION GRAFT DEPLOYMENT CATHETER and filed on Mar. 15, 2000), U.S. Pat. No. 6,660,030 (titled BIFURCATION GRAFT DEPLOYMENT CATHETER and filed on Dec. 22, 2000), or U.S. Pat. No. 6,733,523 (titled IMPLANTABLE VASCULAR GRAFT and filed on Jun. 26, 2001). The entirety of each of the above-listed patents are hereby incorporated by reference as if fully set forth herein.

For example, in some embodiments, the main body graft 12 and/or the branch graft 14 can be expanded using an uncovered (i.e., bare) self-expanding metal frame or a self-expanding metal frame covered with a thin graft material, which can be made from ePTFE, as disclosed in U.S. Pat. No. 6,077,296.

However, the specific design and selection of the materials, shapes, or other aspects for the main body graft 12 or the branch graft 14 of the endoluminal prosthesis 10 is not limited to the designs and configurations disclosed or incorporated by reference herein, but can be based on any suitable variety of materials, shapes, or other aspects of any other suitable endoluminal prostheses. Additionally, the main body graft 12 and/or the branch graft 14 (or any other main or branch graft disclosed herein) can be expanded using a mechanical expander, and be held in the expanded position against the blood vessel wall by the blood pressure within the vessel (i.e., without the use of a stent).

In some embodiments, the main body graft 12 can comprise an expandable metal frame to support the main body graft 12 within the aorta (not illustrated). The frame supporting the main body graft 12 of the endoluminal prosthesis 10 can be formed from a metal or any other suitable material, and can be configured so as to not obstruct the flow of blood through the opening 14b in the branch graft or grafts 14. The metal frame can comprise a self-expandable structure comprising one or more wires forming a zig-zag, tubular shape, as described above with reference to U.S. Pat. Nos. 6,077,296, 6,187,036, 6,197,049, 6,500,202, 6,660,030 and/or 6,733,523. In some embodiments, the metal frame can be formed by laser cutting a tubular structure. Such structures are well known in the art. However, those of skill in the art will recognize that various configurations and constructions of the frame can be used in light of the disclosure herein.

Figure 2:
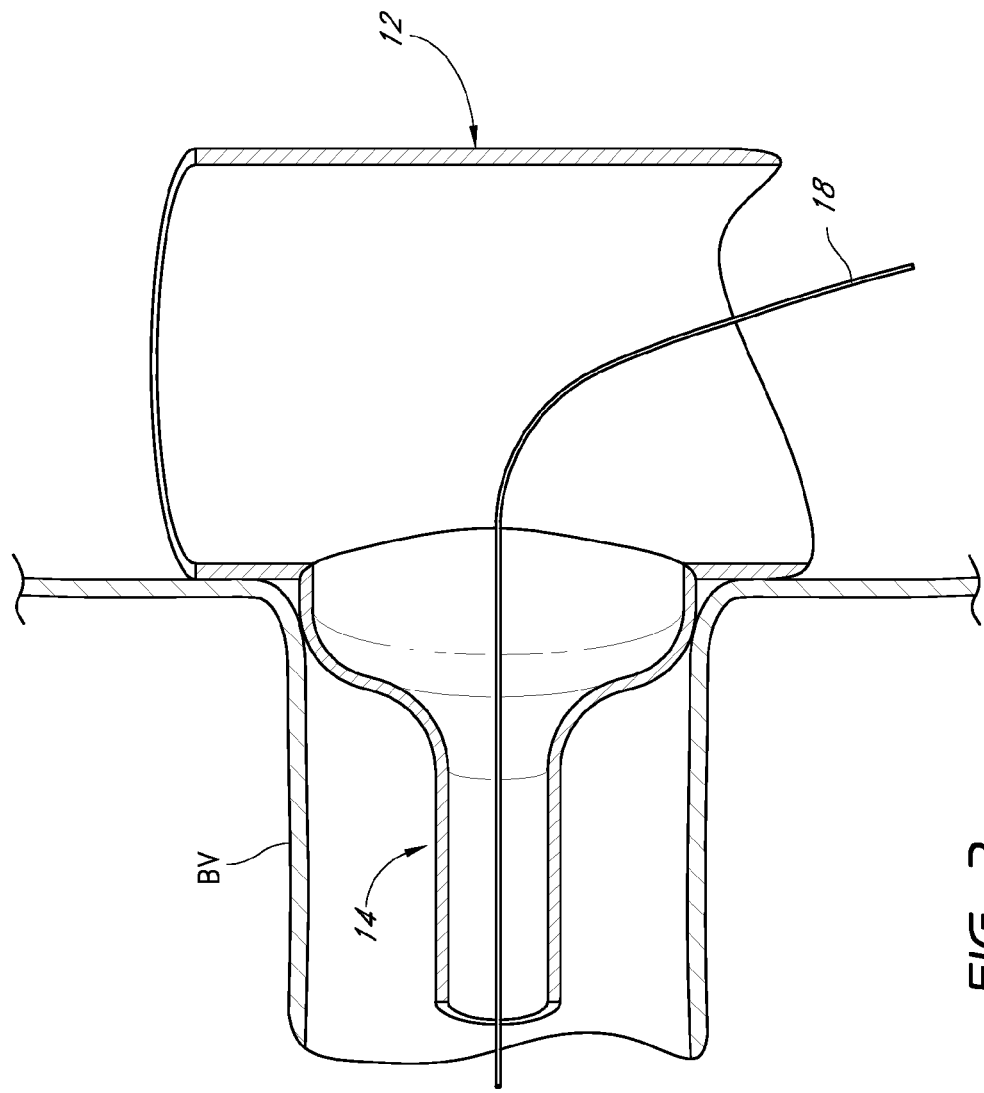
FIG. 2 is a partial section view of a portion of the embodiment of the endoluminal prosthesis illustrated in FIG. 1A, after the branch graft portion of the endoluminal prosthesis has been positioned within a branch artery.
Figure 3:
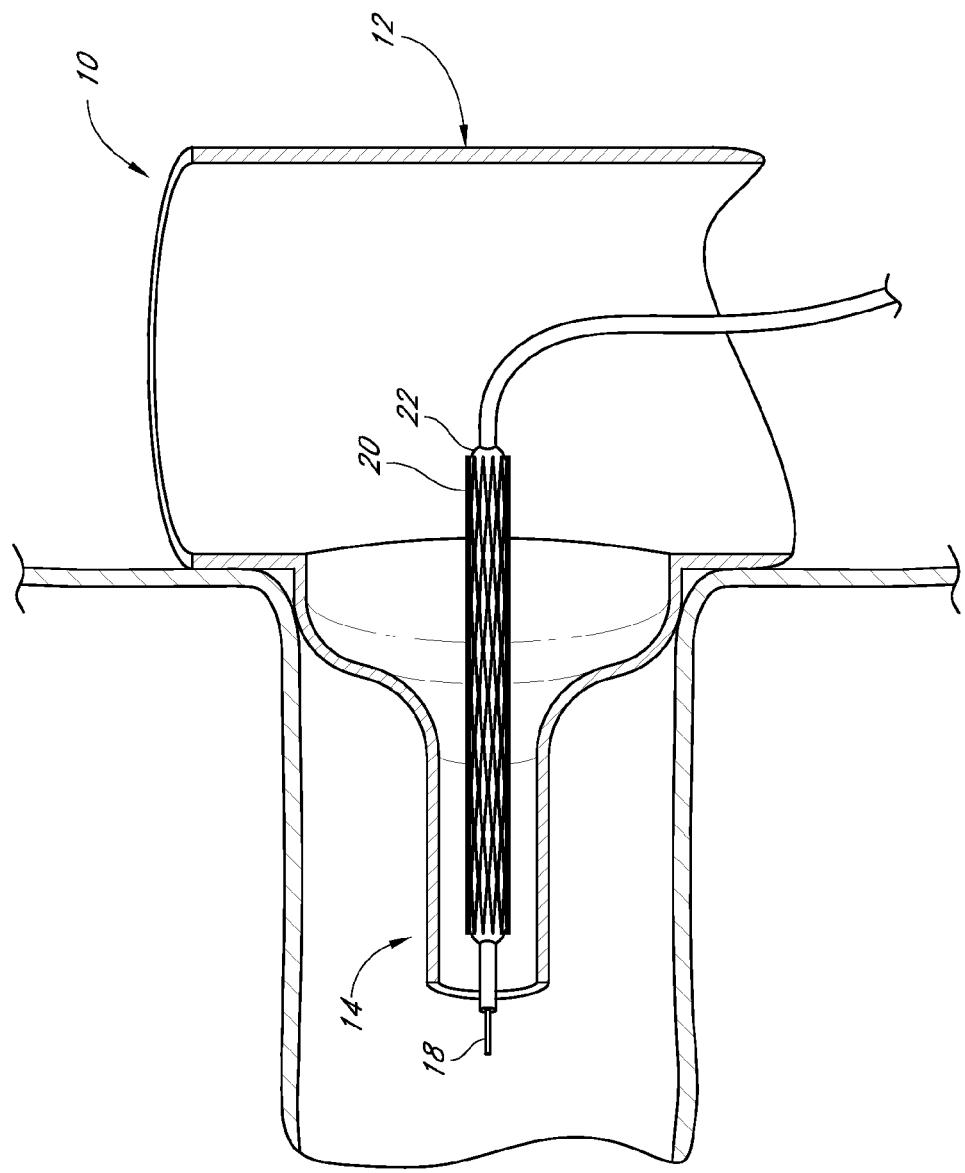
FIG. 3 is a partial section view of a portion of the embodiment of the endoluminal prosthesis illustrated in FIG. 1A, showing a balloon expandable stent being positioned within the partially expanded branch graft of the endoluminal prosthesis.
Figure 4:
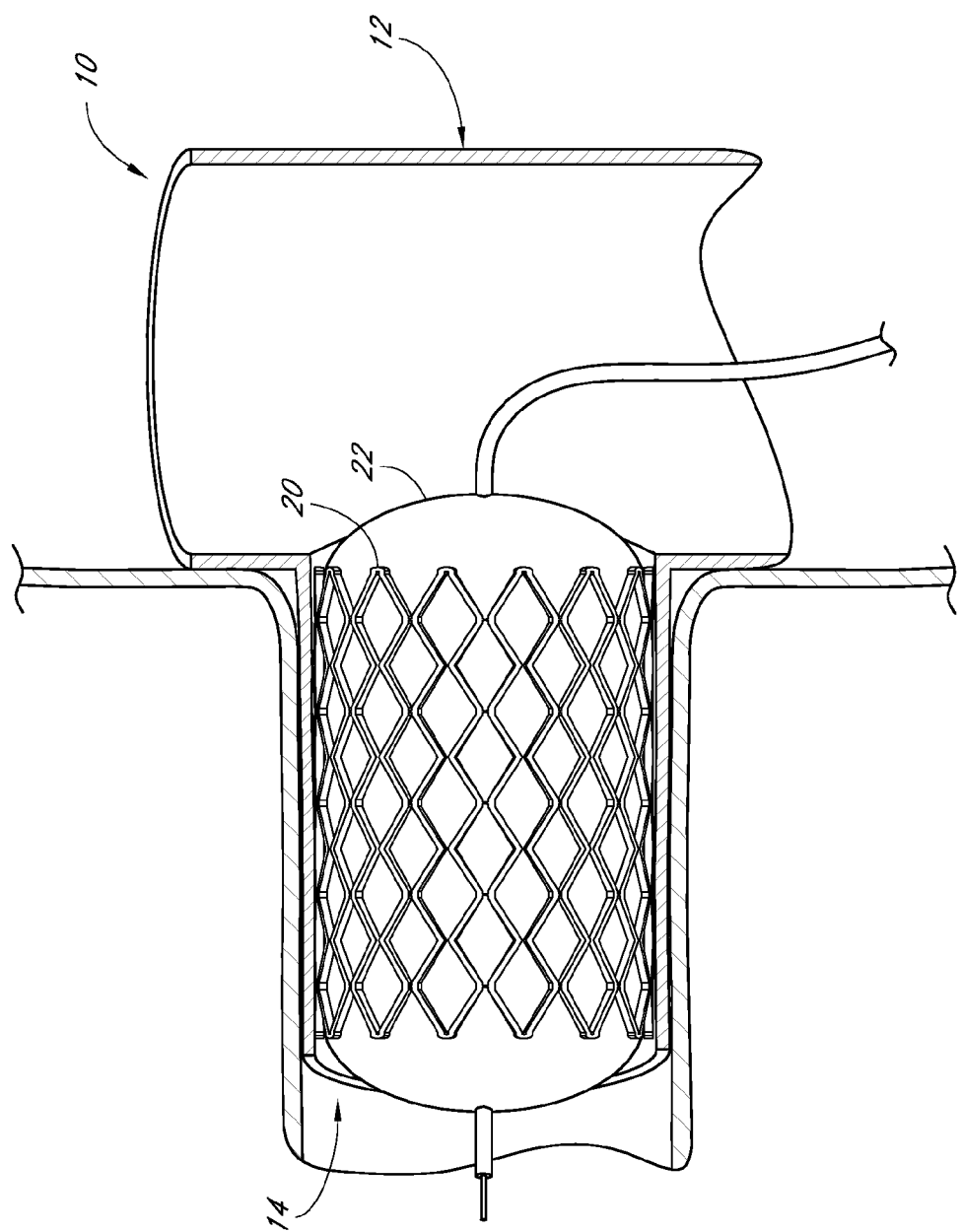
FIG. 4 is a partial section view of a portion of the embodiment of the endoluminal prosthesis illustrated in FIG. 1A, showing a balloon expandable stent being expanded within the branch graft of the endoluminal prosthesis.
Figure 5:
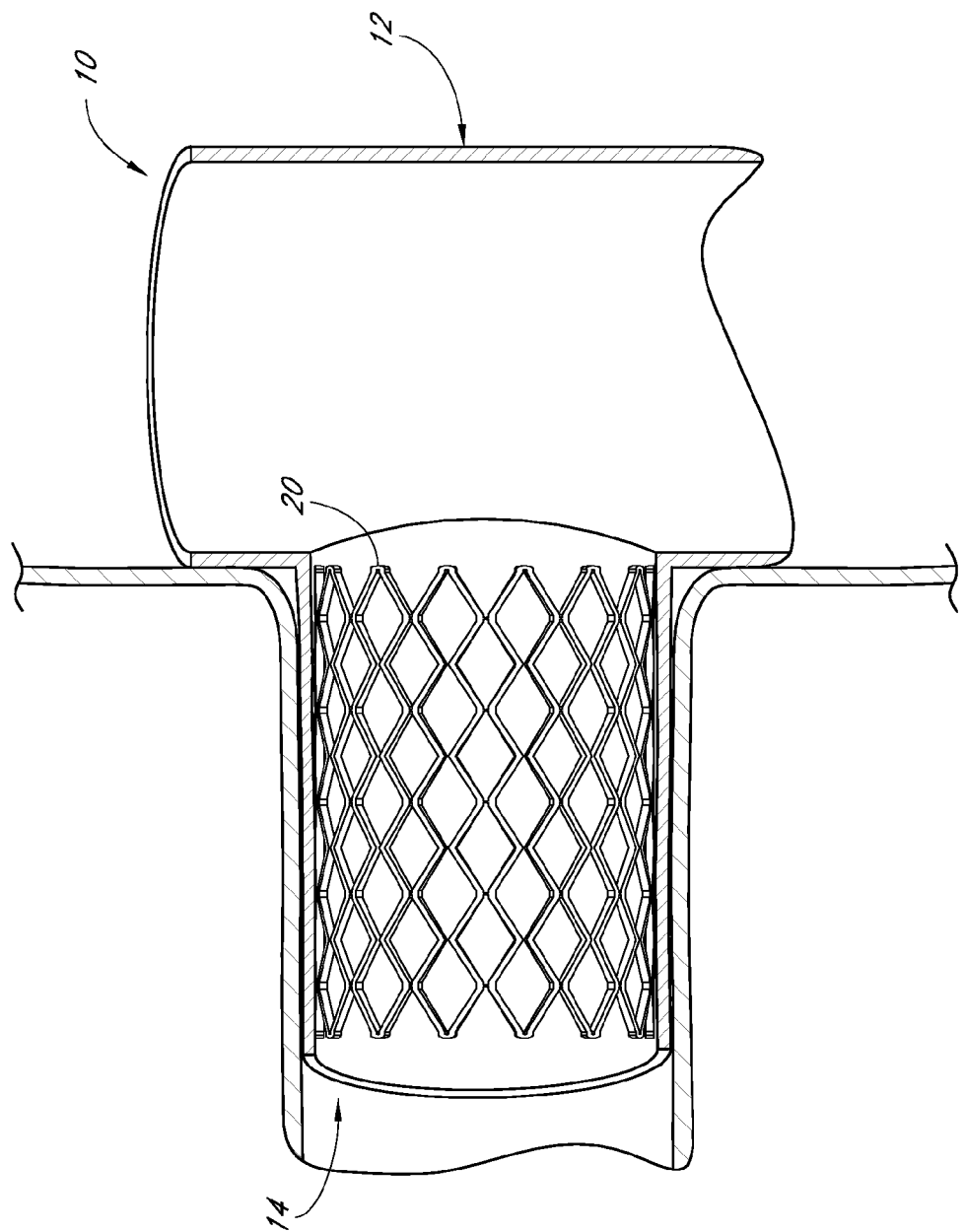
FIG. 5 is a partial section view of a portion of the embodiment of the endoluminal prosthesis illustrated in FIG. 1A, showing an expanded stent positioned within a branch graft of the endoluminal prosthesis.

FIG. 2 is a partial section view of a portion of the embodiment of the endoluminal prosthesis 10 illustrated in FIG. 1A, after the branch graft portion 14 of the endoluminal prosthesis 10 has been positioned within a branch vessel artery (represented by BV in FIG. 2). FIG. 3 is a partial section view of a portion of the embodiment of the endoluminal prosthesis 10 illustrated in FIG. 1A, showing a balloon expandable stent being positioned within the partially expanded branch graft 14 of the endoluminal prosthesis 10. FIG. 4 is a partial section view of a portion of the embodiment of the endoluminal prosthesis 10 illustrated in FIG. 1A, showing a balloon expandable stent being expanded within the branch graft 14 of the endoluminal prosthesis 10. FIG. 5 is a partial section view of a portion of the embodiment of the endoluminal prosthesis 10 illustrated in FIG. 1A, showing an expanded stent positioned within a branch graft 14 of the endoluminal prosthesis 10.

With reference to FIGS. 2-5, one method of positioning and implanting the fully assembled endoluminal prosthesis 10 in the desired aortic location will now be described. After advancing a guidewire 18 through the vasculature into the desired branch vessel BV by known or suitable methods, the partially expanded branch graft 14 of the endoluminal prosthesis 10 can be guided over the guidewire 18 so that the main body graft 12 is positioned within the desired location in the aorta and the branch graft 14 is positioned in the desired branch vessel (represented by BV in FIG. 2).

With reference to FIG. 3, once the partially expanded branch graft 14 is positioned within the desired branch vessel BV, a balloon-expandable stent 20 can be guided over the guidewire 18 and positioned inside the partially expanded branch graft 14. As shown in FIG. 4, the balloon expandable stent 20 can be expanded by the expansion of a balloon 22 positioned within the balloon expandable stent 20. Once the stent 20 of the branch graft 14 has been expanded by the balloon 22, a balloon 22 can be deflated, leaving the expanded stent 20 positioned within the branch graft 14, as illustrated in FIG. 5.

The main body graft 12 and/or branch graft 14 the can be expanded and secured in the desired position by any other suitable method for such. Suitable expansion apparatuses and methods include, but are not limited to, balloon catheters, dilators, and self-expanding stents or stent grafts. Other means of securing the main body graft 12 and/or branch graft 14 may include, without limitation, self-expanding stents, stent grafts, sutures, and staples.

In some embodiments, the stent 20 can be a bare wire stent of any configuration described above or incorporated herein by reference. In some embodiments, the stent 20 can be a graft covered stent, also of any configuration described above or incorporated herein by reference. A graft covered stent can provide a greater degree of safety to the patient by providing a double layer graft system that can be less prone to tearing or other damage.

In some arrangements, after the branch stent 20 and the branch graft 14 have been expanded within the desired branch vessel, the main body graft 12 may thereafter be expanded within the aorta. In some arrangements, the main body graft 12 can be expanded within the aorta prior to expanding the branch stent 14 within the branch vessel BV. The main body graft 12 can be expanded and held in the desired position using a self-expandable stent, or can be expanded and held in position by any other suitable stent device, such as without limitation, a balloon expandable stent. As such, similar to the branch graft 14, the main body graft 12 can be expanded and held in position with a bare metal stent or a covered stent, or any of the stents described or incorporated by reference herein.

Some embodiments of the endoluminal prosthesis 10 can be implanted within the desired vessel in a multistep process, such that an integrated deployment mechanism is not used for such embodiments of the endoluminal prosthesis 10. The expansion and stenting of the branch graft 14 can be performed in a secondary procedure, after the branch graft 14 has been positioned in the desired blood vessel.

Figure 6:
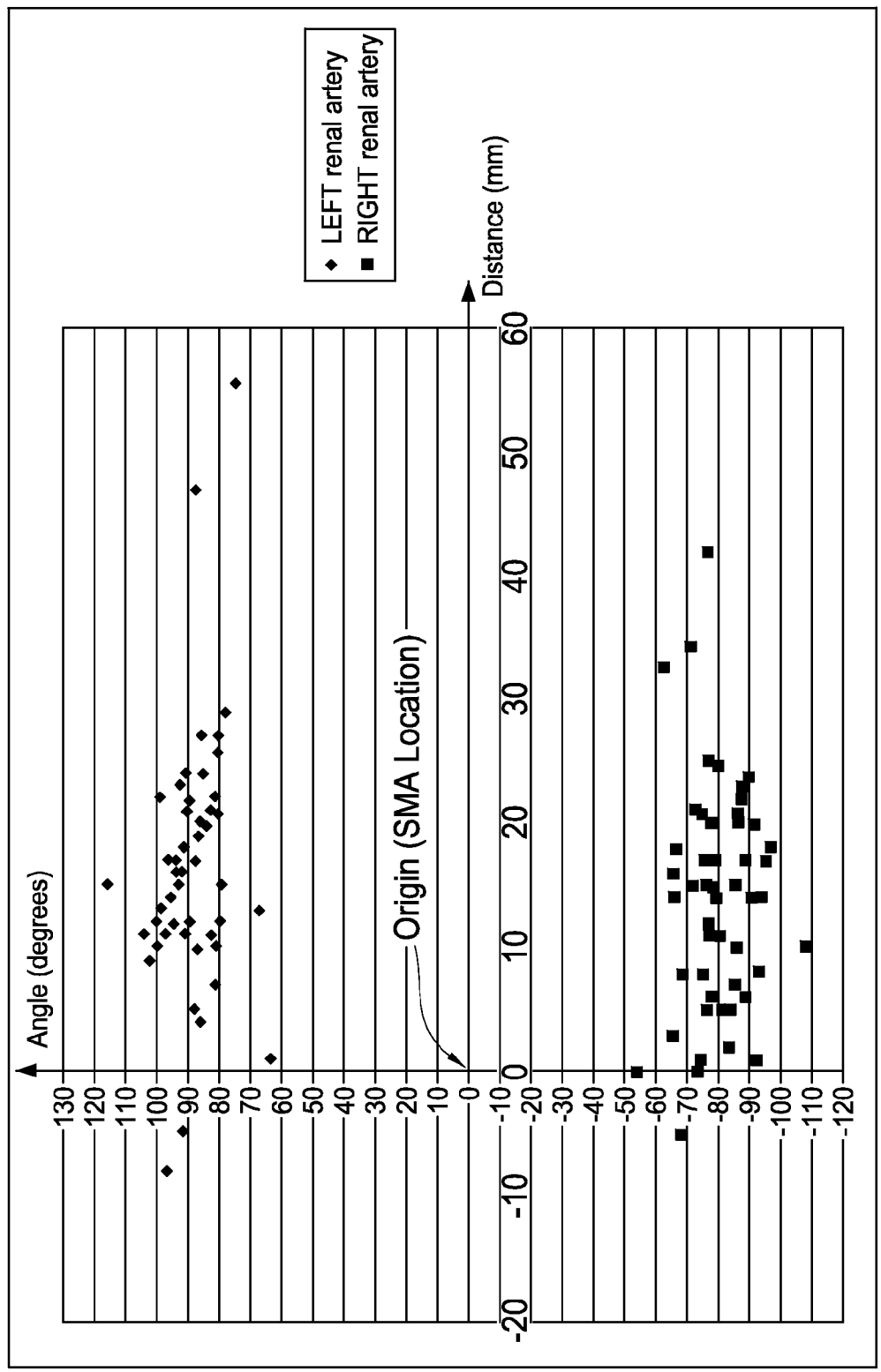
FIG. 6 is a graphical illustration of the location of the two renal arteries with respect to the superior mesenteric artery ("SMA") in 50 patients undergoing an abdominal aortic aneurysm ("AAA") procedure.

As mentioned, in certain situations, several vessels may branch off from the main blood vessel in the location that is desired to be stented. In this case, the endoluminal prosthesis 10 can be formed with multiple branch grafts 14 formed therein or secured thereto. For example, the two renal arteries and the superior mesenteric artery ("SMA") generally branch off from the aorta in close proximity to each other. The positions of the branch vessels generally vary from patient to patient, as shown in FIG. 6, which is a graphical illustration of the location of the two renal arteries with respect to the SMA in 50 patients undergoing an abdominal aortic aneurysm (AAA) procedure. For reference, the SMA is located at the origin of the graph. The locations of the left and right renal arteries are expressed in terms of axial distance from the SMA in millimeters (x-axis), and circumferential angle from the SMA (y-axis). As FIG. 6 illustrates, there is typically a large variability in the locations of the vessels from one patient to the next.

FIG. 6 indicates that, in case of stent grafting across the renal arteries, the small and the large opening are approximately 180 degrees opposite to each other. In some embodiments, the large opening can be sufficiently large to accommodate an axial distance between the renal arteries of between approximately 15 mm and approximately 20 mm, and a circumferential asymmetry of +/−20 degrees. Thus, in some embodiments, the large opening may have a diameter of approximately 20 mm.

Figure 7B:
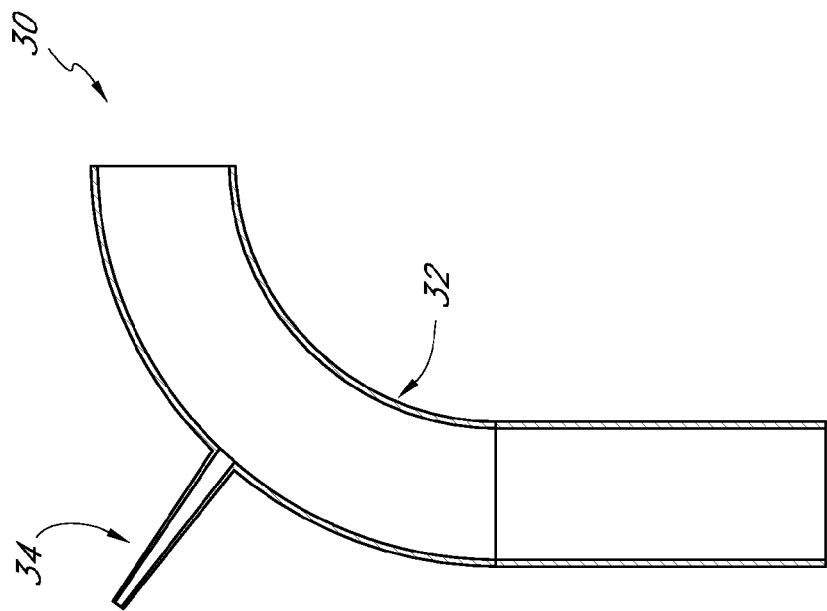
FIGS. 7A and 7B are a front view and a section view, respectively, of another embodiment of an endoluminal prosthesis.
Figure 7A:
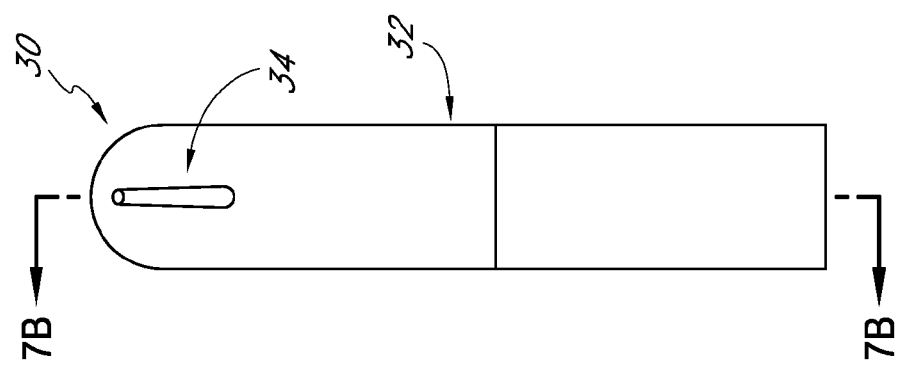

FIGS. 7A and 7B are a front view and a section view, respectively, of another embodiment of an endoluminal prosthesis 30 having a main body graft 32 and a branch graft 34.

Figure 8A:
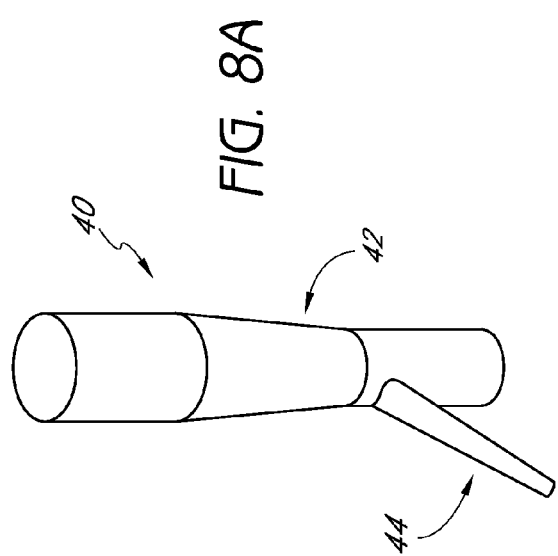
FIGS. 8A, 8B, and 8C are a perspective view, top view, and section view, respectively, of yet another embodiment of an endoluminal prosthesis.
Figure 8C:
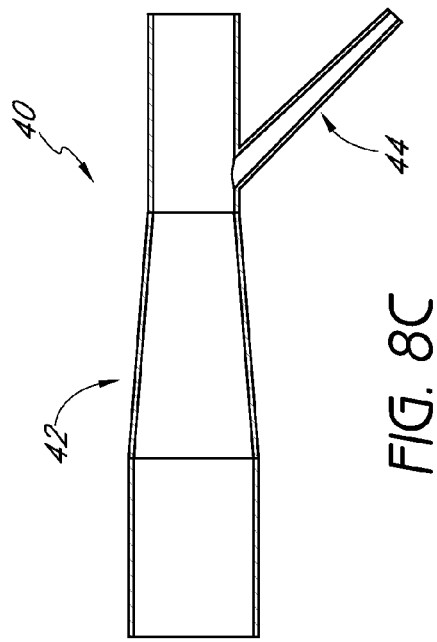
Figure 8B:
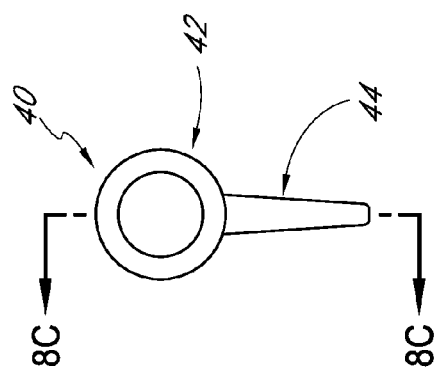

FIGS. 8A, 8B, and 8C are a perspective view, top view, and section view, respectively, of another embodiment of an endoluminal prosthesis 40 having a main body graft 42 and a branch graft 44.

The embodiments of the endoluminal prostheses in FIGS. 7A-8B can be configured for application in portions of the body other than in the portions of the aorta described above. For example, some embodiments of the endoluminal prosthesis 30 illustrated in FIGS. 7A, 7B can be configured for application in a specific artery or arteries. In particular, without limitation, the embodiment of the endoluminal prosthesis 30 illustrated in FIGS. 7A, 7B can be configured for use in the thoracic aorta, with the branch graft 34 configured for positioning within the subclavian artery. As illustrated, in FIGS. 7A, 7B, the main body graft 32 can define curved portion that may be suitable for curved vessels such as that of the subclavian artery. Other aspects of the endoluminal prosthesis 30 can be the same as or similar to any of the other endoluminal prostheses disclosed herein, and the endoluminal prosthesis 30 can be deployed and secured in the desired artery by any of the same methods as described above with respect to endoluminal prosthesis 10.

Similarly, some embodiments of the endoluminal prostheses 40 illustrated in FIGS. 8A, 8B can also be configured for application in a specific artery or arteries. For example, without limitation, the embodiments of the endoluminal prosthesis 40 illustrated in FIGS. 8A, 8B can be configured for use in the iliac artery, with the branch graft 44 configured for positioning within the hypogastric artery or arteries. However, there are many locations in the body that would benefit from a placement of a branch graft systems or endoluminal prostheses disclosed herein to ensure perfusion of branch vessels, and none of the embodiments of the endoluminal prostheses disclosed herein are confined to any particular portion of the body. The examples described with regard to FIGS. 7A-8B merely serve as illustrations of potential applications of such a branch graft system. Other aspects of the endoluminal prosthesis 40 can be the same as or similar to any of the other endoluminal prostheses disclosed herein, and the endoluminal prosthesis 40 can be deployed and secured in the desired artery by any of the same methods as described above with respect to endoluminal prosthesis 10.

The issue of variability in the anatomy has been overcome in the past by providing custom-made fenestrated grafts in which the openings (commonly referred to as fenestrations) are formed in the main body graft, which were generally custom-made to fit vessels of the individual patient. One disadvantage of custom making the fenestrated grafts after examining the individual patients vascular anatomy is that, as mentioned, the patient's anatomy is generally required to be closely examined using imaging scans prior to fabricating the fenestrated graft. Subsequently, image analysis is typically required to be performed to determine the geometrical relationship between the particular patient's main vessel and the branch vessels. This generally required the medical practitioner to individually build or modify the endoluminal prosthesis to create fenestrations at the appropriate location of the branch vessels. The custom-made graft then is generally required to be placed exactly in the correct location in the blood vessel to ensure that the fenestrations are properly aligned with the branch vessel. Another disadvantage is that this can be a multi-step, time consuming procedure. It is not uncommon to require several months to prepare a custom-made graft for the patient. Additionally, the deployment of a custom-made endoluminal prosthesis can be very difficult, typically requiring a high skill level in endovascular procedures.

Figure 9B:
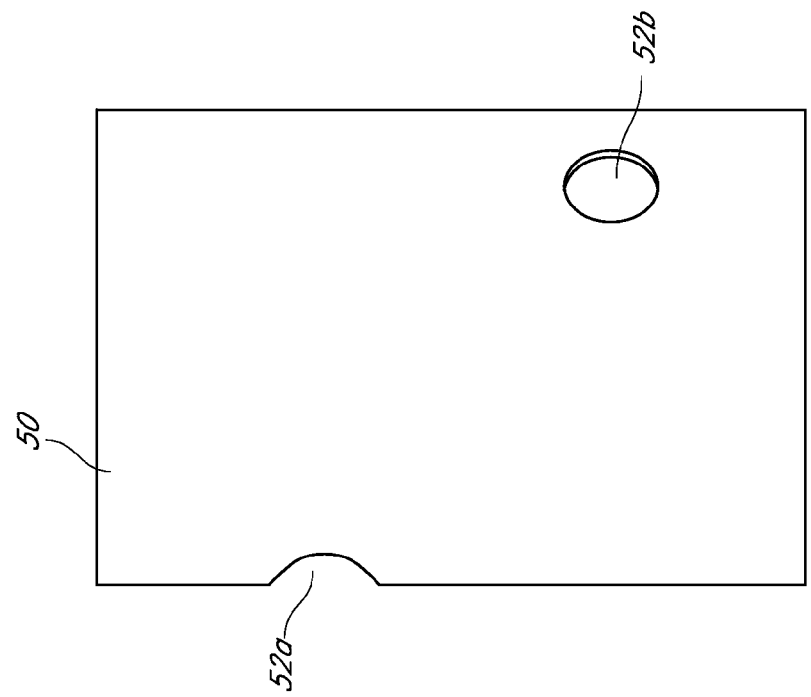
FIGS. 9A and 9B are a perspective view and a side view, respectively, of an embodiment of a fenestrated endoluminal prosthesis.
Figure 9A:
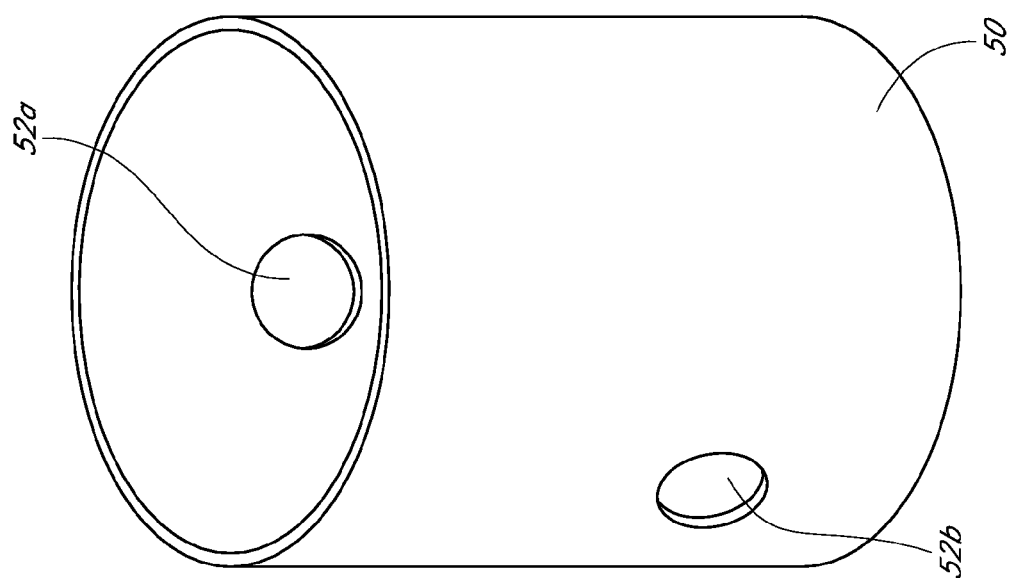

The following embodiments present additional alternatives to the custom-made fenestrated grafts discussed above. FIGS. 9A and 9B are a perspective view and a side view, respectively, of an embodiment of a fenestrated endoluminal prosthesis or graft 50. As illustrated in FIGS. 9A, 9B, the fenestrated graft 50 can have two openings or fenestrations 52a, 52b formed in the main graft 50. Any of a wide ranging variety of fenestrated grafts 50 can be manufactured, each having a different location of the two openings or fenestrations 52a, 52b formed therein so that the doctor can select the appropriately configured fenestrated graft 50 depending on the patient's particular vasculature.

FIGS. 10A and 10B are a perspective view and a side view, respectively, of an embodiment of a fenestrated endoluminal prosthesis 60 (also referred to herein as a first endoluminal prosthesis or graft), which present an alternative to the custom-made fenestrated grafts discussed above. To facilitate and description of some of the embodiments disclosed herein, the placement of the fenestrated endoluminal prosthesis 60 at the renal arteries is described. However, the embodiments of the fenestrated endoluminal prostheses 60 disclosed herein are not limited to this particular location or application. This application merely serves as an example to illustrate the basic aspects of the fenestrated endoluminal prosthesis 60.

In some embodiments, the endoluminal prosthesis 60 can comprise a main body 62 and first and second openings 64, 66, respectively. The main body 62 can have an inside surface 62a and an outside surface 62b. In some embodiments, the endoluminal prosthesis 60 can comprise any suitable or desired number of openings. For example, without limitation, the endoluminal prosthesis 60 can have one or more openings or cutouts (not illustrated) in addition to the openings 64, 66 illustrated in FIGS. 10A, 10B to account for other renal or branch arteries that may otherwise be covered by the main body 62 of the endoluminal prosthesis 60.

In the embodiment of the endoluminal prosthesis 60 illustrated in FIGS. 10A, 10B, the openings 64, 66 can be positioned at mutually or diametrically opposing locations. However, the openings 64, 66 can be positioned at any desired or suitable axial or radial position. Additionally, in the embodiment of the endoluminal prosthesis 60 illustrated in FIGS. 10A, 10B, the openings 64, 66 can have a circular shape. However, the openings 64, 66 can have any desired or suitable shape, including square, rectangular, polygonal, or otherwise.

Further, in the illustrated embodiment where each of the openings are generally circular, the diameter of the second opening 66 can be approximately four times greater than the diameter of the first opening 64. In some embodiments, the diameter of the second opening 66 can be between approximately two times greater and approximately four times greater, or between approximately four times greater and approximately six times or more greater than the diameter of the first opening 64. Additionally, in some embodiments, the second opening 66 can be configured to be as large as is possible to cover a wide range of branch vessel anatomies. As the size of the second opening 66 is increased, the potential to treat a large range of branch vessel anatomies is also increased.

Similarly, in some embodiments where the openings are non-circular, the width and/or height of the second opening 66 can be approximately four times greater than the width and/or height of the first opening 64. In some embodiments, the width and/or height of the second opening 66 can be between approximately two times greater and approximately four times greater, or between approximately four times greater and approximately six times or more greater than the width and/or height of the first opening 64.

In some embodiments, similar to any other prosthesis disclosed herein, the prosthesis 60 can be self-expanding, balloon expandable, or can be of any other suitable configuration. The openings 64, 66 can be configured to be positioned adjacent to the two renal arteries. The first opening 64 can approximately match the size of the first renal artery, while the second opening 66 can be substantially larger that the first opening 64. As will be described in greater detail below, the size of the second opening 66 can be greater than the size of the first opening 64 to account for the variability in the location of the second renal artery with respect to the first renal artery. In this configuration, the endoluminal prosthesis 60 can be positioned within the patient's vasculature so that the main body 62 of the endoluminal prosthesis 60 does not cover the second renal when the first opening 64 of the main body 62 is aligned with the patient's first renal artery.

Figure 11B:
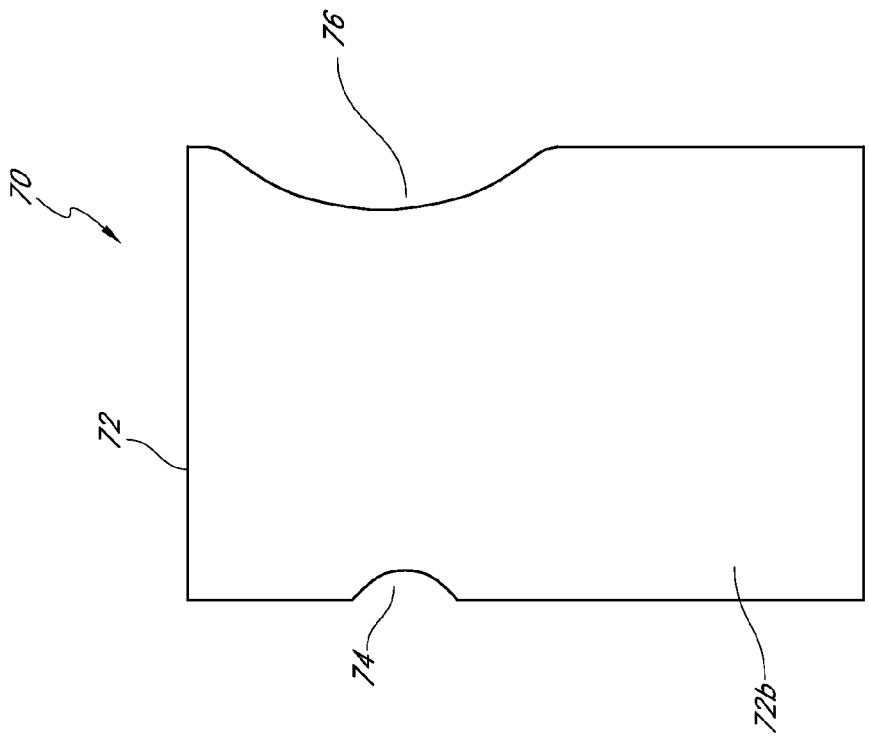
FIGS. 11A and 11B are a perspective view and a side view, respectively, of another embodiment of a fenestrated endoluminal prosthesis.
Figure 11A:
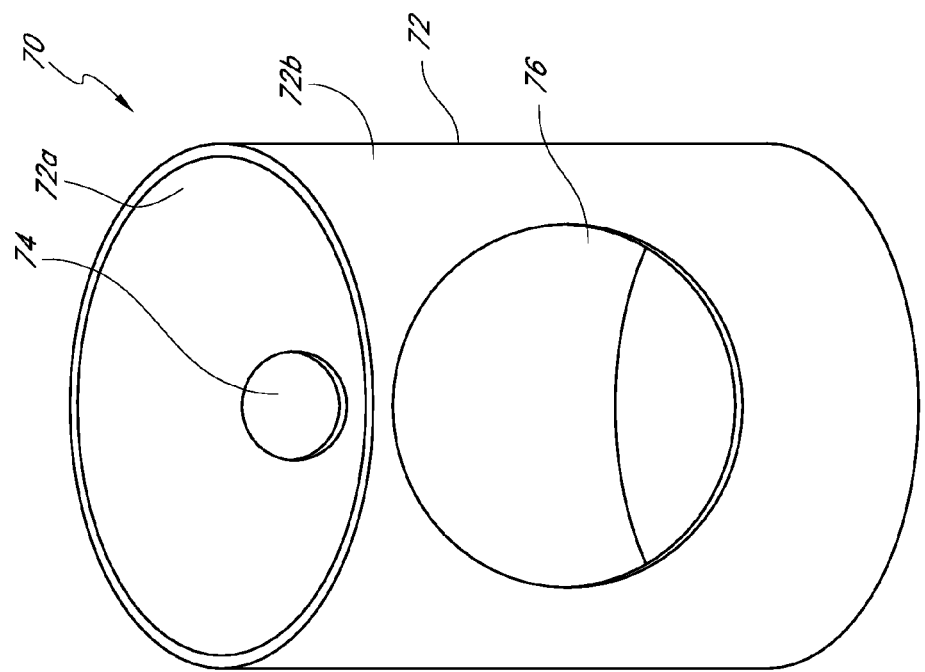

As will be described in greater detail below, to seal the area around the second renal artery after the first endoluminal prosthesis 60 has been positioned in the patient's vasculature, another fenestrated endoluminal prosthesis 70 (also referred to herein as a second endoluminal prosthesis or graft) comprising a main body 72, a first or smaller opening 74, and a second or larger opening 76, can be inserted into the patient's vasculature on the inside of the first endoluminal prosthesis 60. FIGS. 11A and 11B are a perspective view and a side view, respectively, of the embodiment of the fenestrated endoluminal prosthesis 70. The main body 72 can have an inside surface 72a and an outside surface 72b.

The first or smaller opening 74 of the second endoluminal prosthesis 70 can be positioned within the patient's vasculature so as to be aligned with the patient's second renal artery. The second or larger opening 76 of the second endoluminal prosthesis 70 can ensure that the first renal artery is not covered by the main body 72 of the second endoluminal prosthesis 70. The second, larger opening 66 in the first endoluminal prosthesis 60 and the second, larger opening 76 in the second endoluminal prosthesis 70 can allow for greater variability in the location of the renal arteries, without requiring a medical practitioner to custom make the prosthesis.

In particular, after the first endoluminal prosthesis 60 has been positioned in the patient's vasculature so that the outside surface 62b can expand against and contact the walls of the patient's artery and so that the first or smaller opening 64 is approximately aligned with the first renal artery and the second or larger opening 66 is sufficiently aligned with the second renal artery so that the main body 62 does not cover the second renal artery, the second endoluminal prosthesis 70 can be positioned within the patient's vasculature so that the first or smaller opening 74 is approximately aligned with the patient's second renal artery and the second or larger opening 76 is sufficiently aligned with the first renal artery so that the main body 72 does not cover the first renal artery. The second endoluminal prosthesis 70 can then be expanded so that the outside surface 72b of the main body 72 of the second endoluminal prosthesis 70 is in contact with the inside surface 62a of the main body 62 of the first endoluminal prosthesis 60.

In some embodiments, the second endoluminal prosthesis 70 can be the same as or similar to the first endoluminal prosthesis 60 including, but not limited to, having the same number, size, and location of the openings as are in the first endoluminal prosthesis 60. In some embodiments, the second endoluminal prosthesis 70 can have a different configuration as compared to the first endoluminal prosthesis 60 including, but not limited to, having a different number, size, and/or location of the openings that are formed in the main body 72 of the second endoluminal prosthesis 70.

Again, the size and shape of the openings 64, 66, 74, 76 are not limited to the illustrations or the description set forth above, but can be any suitable size or shape, or can be positioned at any suitable location on the endoluminal prosthesis 60, 70, respectively. Additionally, the size, shape, or other aspects of the configuration of the endoluminal prostheses 60, 70 are not limited to the specific embodiments described or illustrated herein. The endoluminal prostheses 60, 70 can comprise any suitable size, shape, including openings or cutouts (i.e., scallops) formed in the proximal and/or distal ends thereof or other aspects of other suitable configurations known or later developed in the field including, but not limited to, other known expandable non-bifurcated and bifurcated prostheses. For example, without limitation, in some embodiments, the main body 62, 72 of the prostheses 60, 70, respectively, can comprise any of the materials, features, or other aspects of the embodiments of the endoluminal vascular prostheses disclosed in U.S. Pat. Nos. 6,077,296, 6,187,036, 6,197,049, 6,500,202, 6,660,030 and/or 6,733,523, the entirety of which are hereby incorporated by reference as if fully set forth herein.

Without limitation, in some embodiments, the main body 62, 72 of the endoluminal prostheses 60, 70 may comprise any of the materials, shapes, or other aspects of the polymeric sleeves and/or the tubular wire supports disclosed in U.S. Pat. Nos. 6,077,296, 6,187,036, 6,197,049, 6,500,202, 6,660,030 and/or 6,733,523. However, the specific design and selection of the materials, shapes, or other aspects for each of the main bodies 62, 72 of the endoluminal prostheses 60, 70 are not limited to those set forth in patents set forth above, but can be based on any suitable variety of materials, shapes, or other aspects of any other suitable endoluminal prostheses. In addition, the techniques and constructions of U.S. Pat. Nos. 6,187,036, 6,197,049, 6,500,202, 6,660,030 and/or 6,733,523, the entire contents of which are hereby incorporated by reference herein, can also be used and/or adapted for use with the main body 62, 72.

Figure 12:
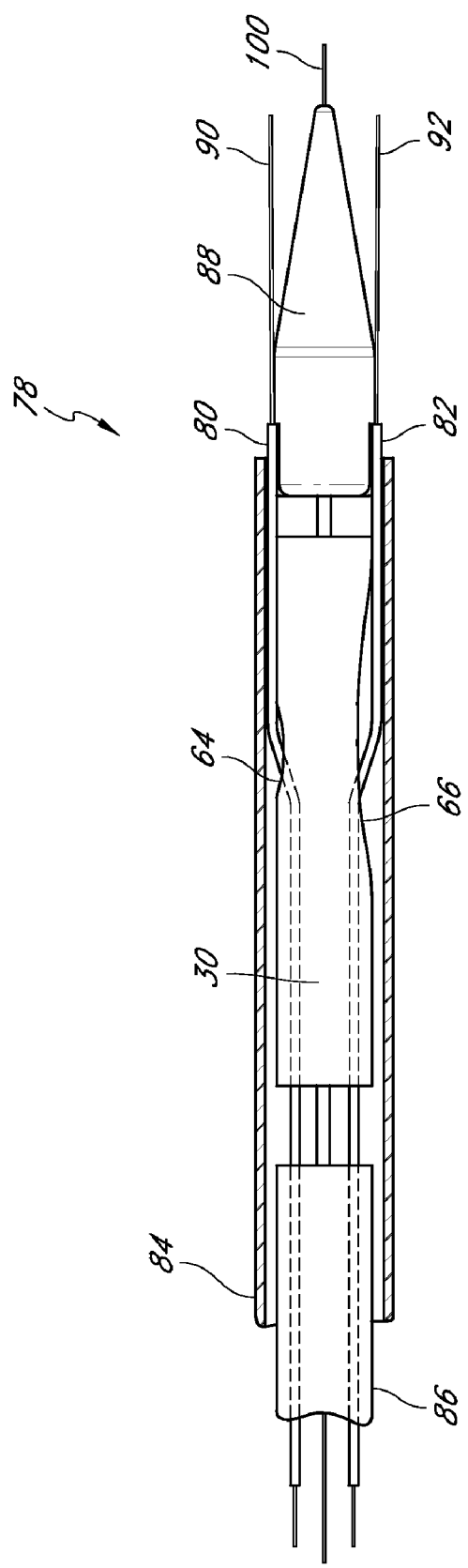
FIG. 12 is a partial section view of the endoluminal prosthesis illustrated in FIGS. 10A, 10B positioned within an embodiment of a delivery catheter.
Figure 13:
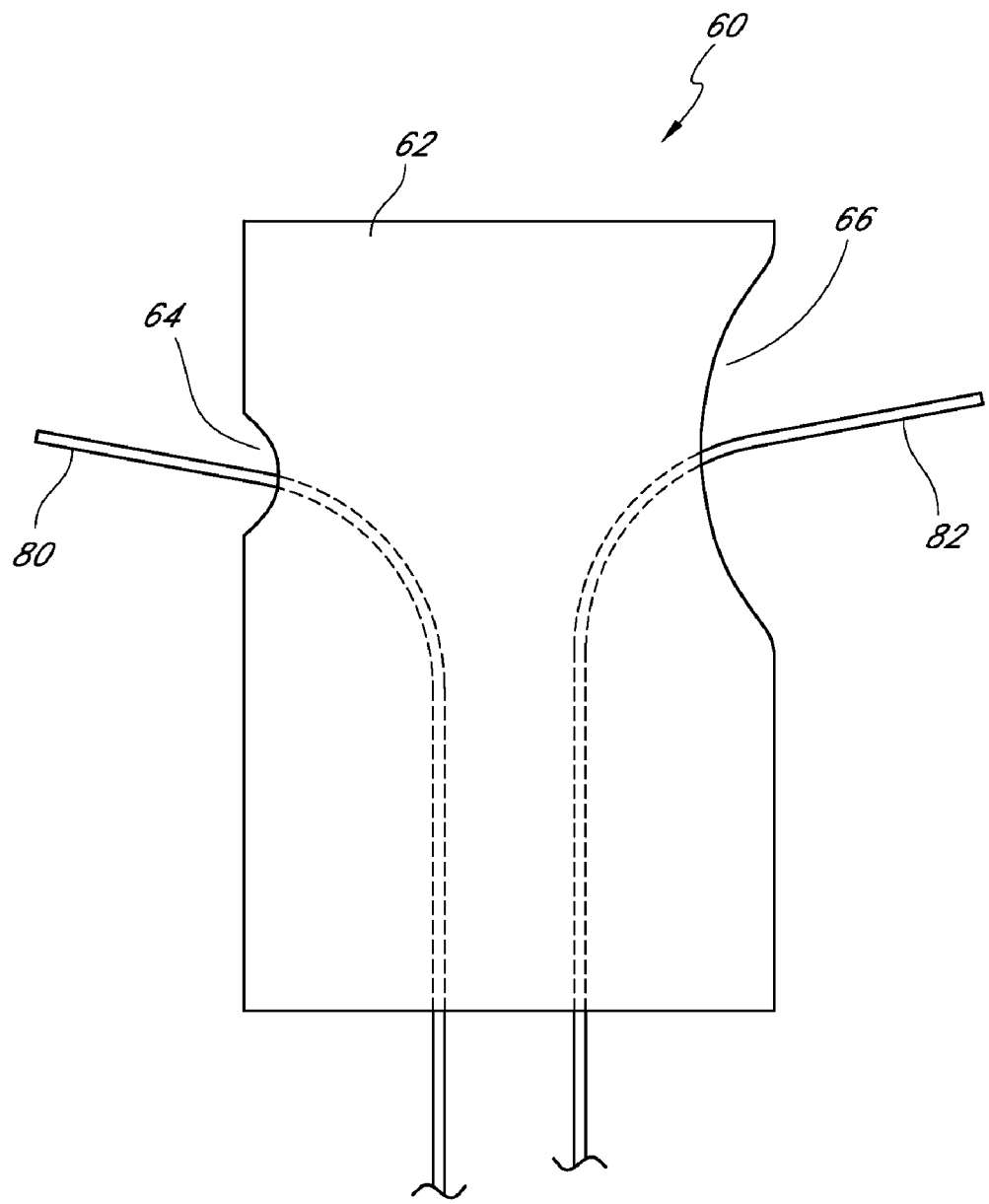
FIG. 13 is a side view of the embodiment of the endoluminal prosthesis illustrated in FIGS. 10A, 10B before the endoluminal prosthesis is placed in a delivery catheter.
Figure 14:
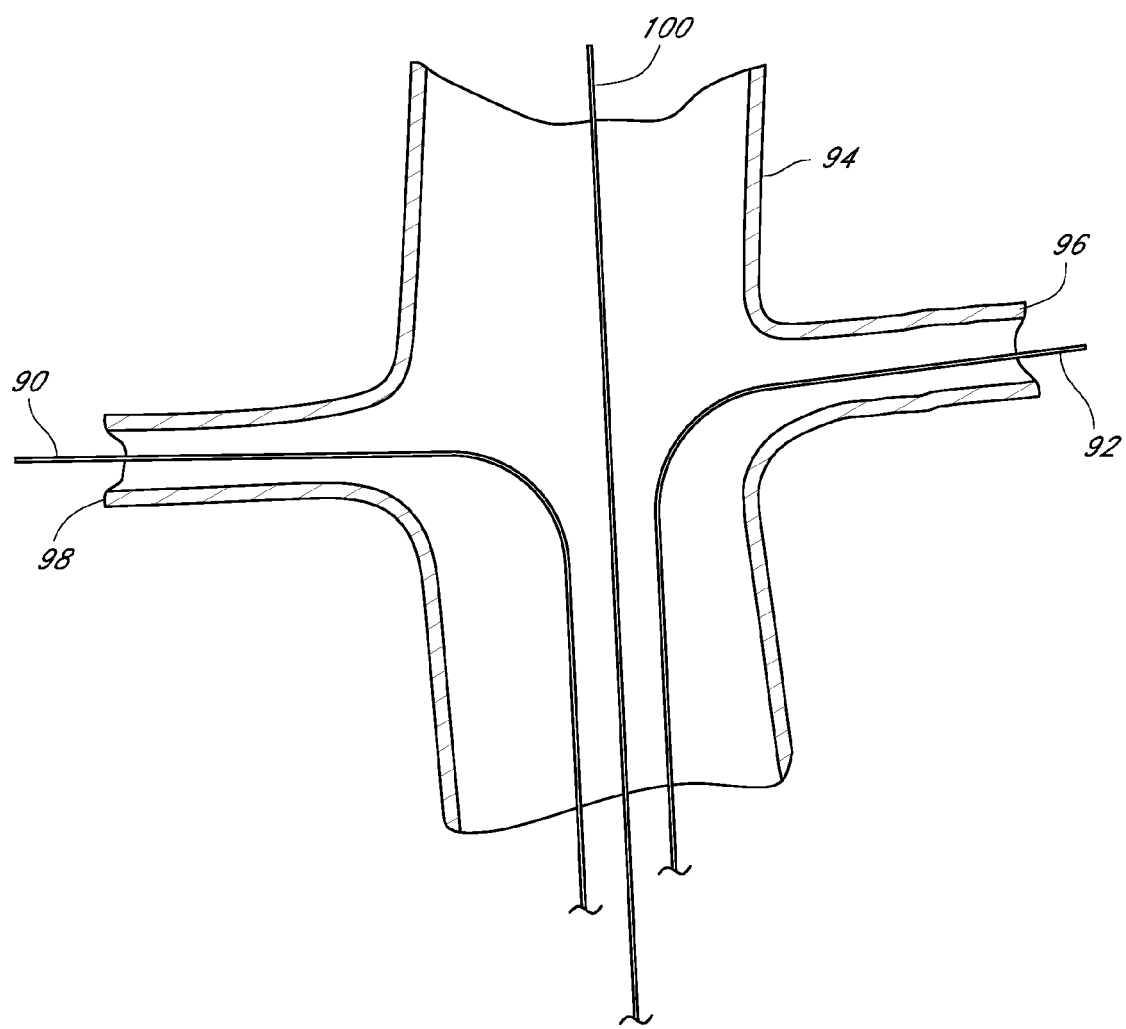
FIG. 14 is a partial section view of a patient's vasculature illustrating guidewires inserted through the abdominal aortic and into the renal arteries.

With reference to FIGS. 12-19, the deployment of the fenestrated endoluminal prosthesis system described above will be described in greater detail. FIG. 12 is a partial section view of the endoluminal prosthesis 60 illustrated in FIGS. 10A, 10B positioned within an embodiment of a delivery catheter 78. FIG. 13 is a side view of the embodiment of the endoluminal prosthesis 60 illustrated in FIGS. 10A, 10B before the endoluminal prosthesis 60 is placed in a delivery catheter 78. With reference to FIGS. 12, 13, the hollow guidewires 80, 82 can be placed through the openings 64, 66, respectively, of the endoluminal prosthesis 60. In some embodiments, the guidewires 80, 82 can be made from a plastic extrusion or metal braids. For example, in some embodiments, the hollow guidewires 80, 82 can be made from braided Nitinol wire. In some embodiments, the outer diameter of the guidewires 80, 82 can be approximately 0.035 in and the lumen of the guidewire can be approximately 0.016 in to accommodate a second 0.014 in guidewire. In some embodiments, the guidewires 80, 82 can be configured to pass over a 0.018 in or any other suitable guidewire. FIG. 14 is a partial section view of a patient's vasculature illustrating guidewires 90, 92 inserted through the abdominal aortic 94 and into the renal arteries 96, 98, respectively.

In some embodiments the guidewires 80, 82 can support balloons on the distal end of the guidewires 80, 82. The balloons can be inflated in the branch vessel to removably anchor or support the guidewire 80, 82 against the vessel wall and prevent inadvertent removal of the guidewires from the branch vessels during the deployment procedure. In some embodiments, for example, one or more occlusion balloon catheters can be used. Other anchoring mechanisms can be attached to the guidewire, such as, without limitation, hooks, to removably secure one or more of the guidewires 80, 82 within or to the vessel.

Additionally, in some embodiments, one of more of the guidewires disclosed herein (such as, without limitation, guidewires 80, 82) can have a coiled distal end portion. The coiled distal end portion can be configured to be insertable into a branch vessel and can be biased to remain in the branch vessel. In particular, in some embodiments, the size or diameter of the coils can be greater than the inside diameter of the branch vessel so as to bias the coiled portion to remain within the branch vessel when the proximal end of the guidewire is retracted. In this configuration, proximal retraction of the guidewire can cause a proximal end of the coil to unravel, allowing a portion of the coiled portion of the guidewire to be unraveled and retracted while the remaining portion of the coiled portion can remain within the branch vessel. This configuration can inhibit the distal end portion of the guidewire from being inadvertently removed from the branch vessel. To completely remove the coiled distal end portion from the branch vessel, the guidewire can be retracted until the entire coiled portion is unraveled and retracted.

In some embodiments, the length of the coiled portion can be approximately 6 cm. In some embodiments, the length of the coiled portion can be between approximately 3 cm or less and approximately 5 cm, or between approximately 5 cm and approximately 7 cm, or between approximately 7 cm and approximately 9 cm or more, or from or to any values in these ranges. In some embodiments, the unraveled length of the coiled portion can be approximately 20 cm. In some embodiments, the unraveled length of the coiled portion can be between approximately 10 cm or less and approximately 15 cm, or between approximately 15 cm and approximately 20 cm, or between approximately 20 cm and approximately 25 cm or more, or from or to any values in these ranges.

However, the guidewires 80, 82 or any other guidewires disclosed herein can have any desired or suitable configuration. For example, the guidewires 80, 82 or any other guidewires disclosed herein can have the same or similar materials, configurations, methods of fabrication, and other aspects or details as the hollow guidewires set forth in U.S. Patent Application Publication No. US 2004-0098087 A1, titled DUAL WIRE PLACEMENT CATHETER (application Ser. No. 10/706,660), filed on Nov. 12, 2003, and U.S. application Ser. No. 11/623,022, titled DUAL CONCENTRIC GUIDEWIRE AND METHODS OF BIFURCATED GRAFT DEPLOYMENT, filed on Jan. 12, 2007, the entirety of both of which are incorporated by reference herein as if fully set forth herein.

With reference to FIG. 12, the collapsed endoluminal prosthesis 60 can be supported within the outer sheath 84 of the delivery catheter 78 in the space between the catheter shaft 86 and the catheter tip 88. In some embodiments, the hollow guidewires 80, 82 can slide through openings or lumens in the catheter shaft 86. Alternatively, in some embodiments, the hollow guidewires 80, 82 can be fixed to the catheter shaft 86.

The hollow guidewires 80, 82 can pass through the outer sheath 84 from the proximal end of the delivery catheter 78 to the distal end of the delivery catheter 78. Each of the hollow guidewires 80, 82 can be configured to receive or allow the insertion of 0.014 in guidewire therethrough. In this configuration, the hollow guidewires 80, 82 can pass over guidewires 90, 92 that can be pre-placed in the appropriate vasculature.

Figure 15:
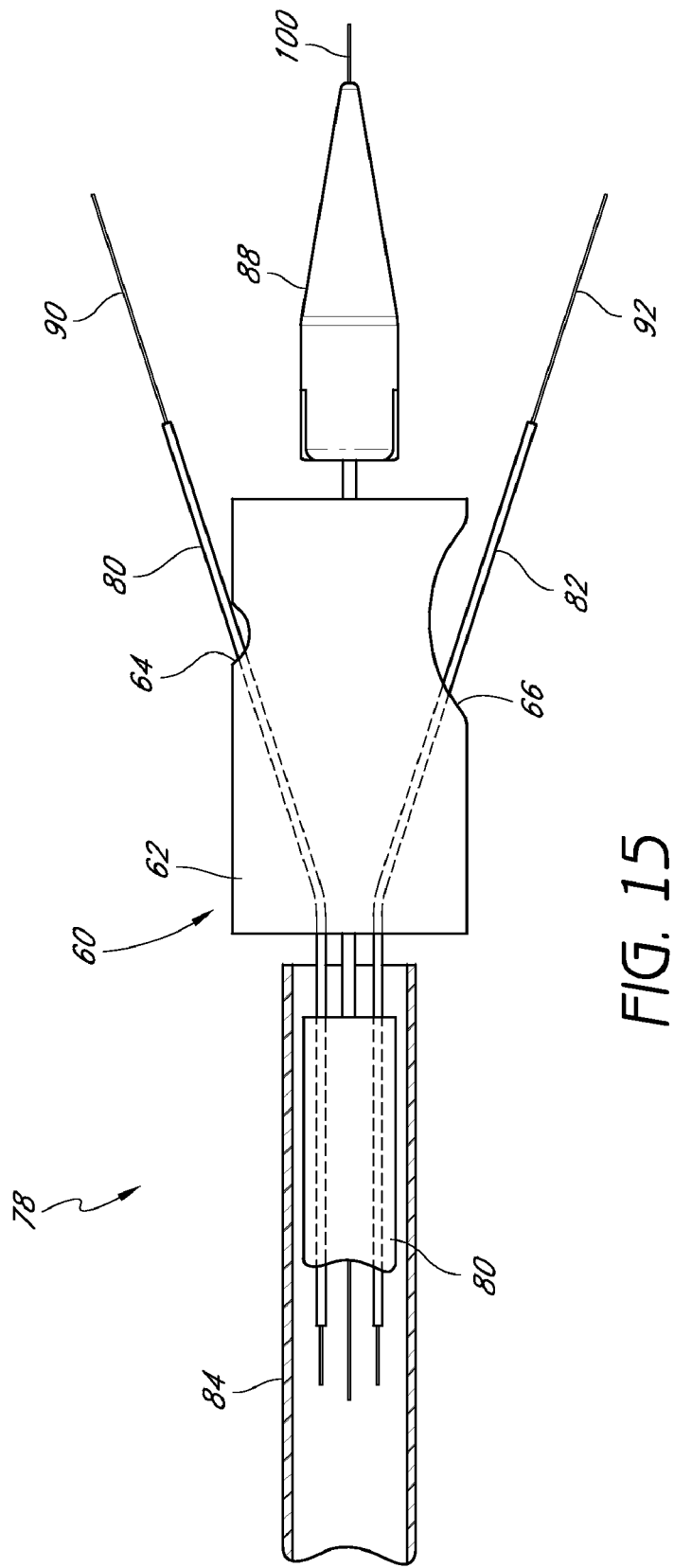
FIG. 15 is a perspective view of the embodiment of the endoluminal prosthesis illustrated in FIGS. 10A, 10B in the deployed or expanded state.

In this configuration, the endoluminal prosthesis 60 can be retained in the delivery catheter 78 by the outer sheath 84. As will be described in greater detail, retraction of the outer sheath 84 can deploy the endoluminal prosthesis 60. With the outer sheath 84 retracted, the endoluminal prosthesis 60 can expand either by self-expansion, balloon expansion, or by any other suitable method or mechanism. FIG. 15 is a perspective view of the embodiment of the endoluminal prosthesis 60 illustrated in FIGS. 10A, 10B in the deployed or expanded state (i.e., after the outer sheath 84 of the catheter 78 has been retracted and of the endoluminal prosthesis 60 has been expanded). FIG. 15 also shows the guidewires 80, 82 passing through the openings 64, 66 respectively. As can be seen in FIG. 15, in some embodiments, the catheter 78 can have three lumens through at least a portion of the catheter 78, each of the three lumens configured to receive a guidewire. Having three lumens through at least a portion of the catheter 78 can prevent twisting of the guidewires, so as to ensure proper deployment.

As again illustrated in FIG. 15, each of the 0.014 in guidewires 90, 92 can be passed through the hollow guidewires 80, 82, respectively. Therefore, before placing the endoluminal prosthesis 60 across the renal arteries, the guidewires 90, 92 can be maneuvered into the target vessels, as shown in FIG. 14, which is a partial section view of a patient's vasculature illustrating guidewires 90, 92 inserted through the abdominal aortic 94 and into the renal arteries 96, 98, respectively.

As illustrated in FIG. 14, third guidewire 100 can be positioned in the aorta 94 at the same time that the 0.014 in guidewires 90, 92 can be placed in the left and the right renal arteries 96, 98, respectively. The delivery catheter 78 can then be passed over guidewire 100 into the aorta. The hollow guidewires 80, 82 of the delivery system can track over the guidewires 90, 92 into the renal arteries until the endoluminal prosthesis 60 is positioned in the desired location.

Figure 16:
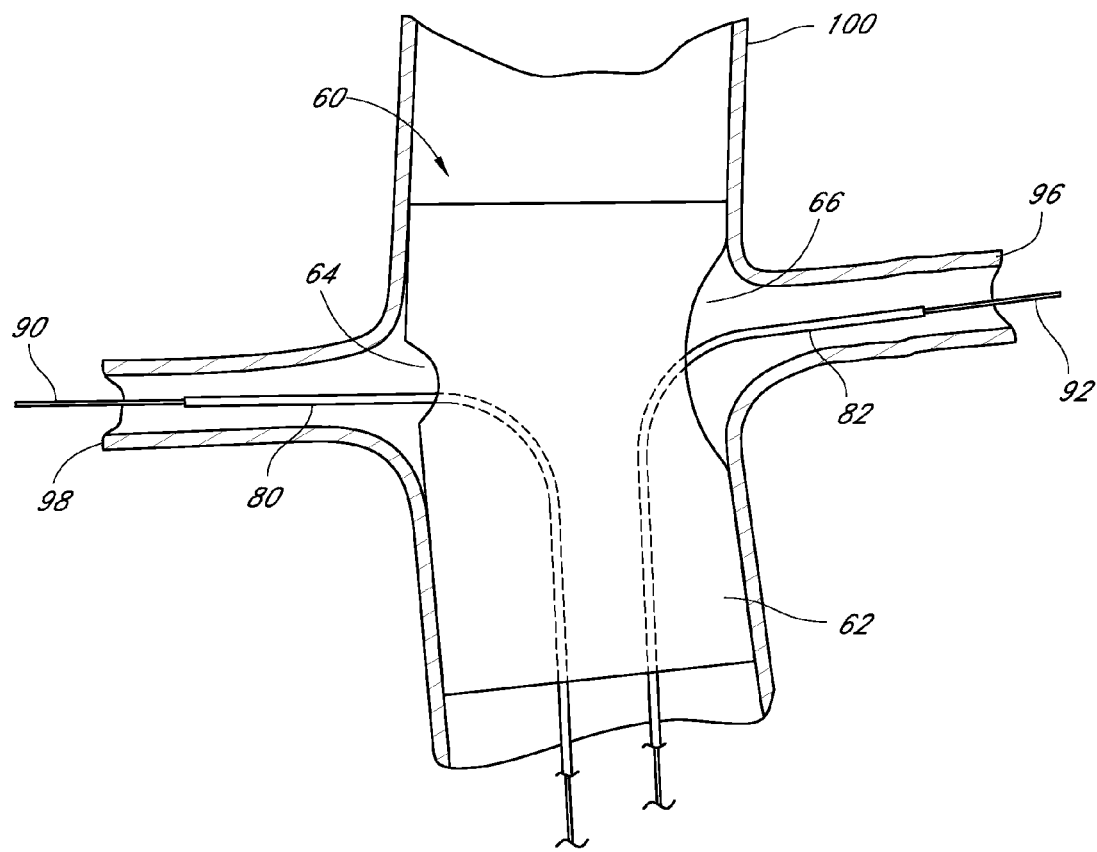
FIG. 16 is a partial section view of a patient's vasculature illustrating the endoluminal prosthesis illustrated in FIGS. 10A, 10B deployed in the desired position within the patient's vasculature, after the components of the delivery system except for the guidewires have been retracted from the patient's vasculature.

FIG. 16 is a partial section view of a patient's vasculature illustrating the endoluminal prosthesis 60 deployed in the desired position within the patient's vasculature, after the components of the delivery catheter 78 except for the guidewires 80, 82 have been retracted from the patient's vasculature. As has been described, the hollow guidewire 80 can pass over the guidewire 90 through the opening 64 into the right renal artery 98. The hollow guidewire 82 can pass over the guidewire 92 through the opening 66 into the left renal artery 96.

In some embodiments, sutures or markers made from an RO material can be sewn into or attached to the endoluminal prosthesis 60 or any other prosthesis disclosed herein adjacent to the openings formed therein or at any other suitable location to assist the medical practitioner in visualizing the location of the prosthesis relative to the patient's vasculature. For example, without limitation, RO sutures can be sewn into the main body 62 of the endoluminal prosthesis 60 around each of the openings 64, 66 and/or near the end portion or portions of the main body 62. Alternatively, RO markers can be sewn to or otherwise attached to the main body of the endoluminal prosthesis 60 or any endoluminal prosthesis at any suitable position.

Figure 17:
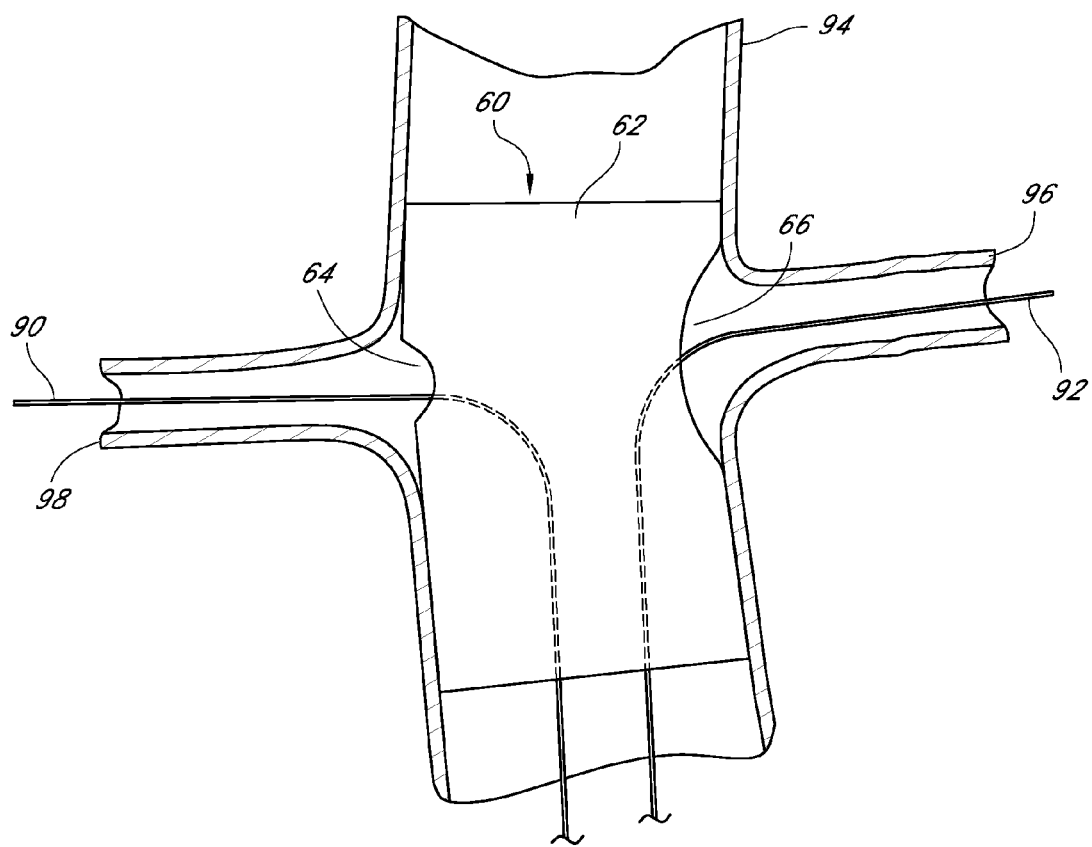
FIG. 17 is a partial section view of a patient's vasculature illustrating the endoluminal prosthesis illustrated in FIGS. 10A, 10B deployed in the desired position within the patient's vasculature, after all of the components of the delivery system have been retracted from the patient's vasculature.

FIG. 17 is a partial section view of a patient's vasculature illustrating the endoluminal prosthesis 60 illustrated in FIGS. 10A, 10B deployed in the desired position within the patient's vasculature, after all of the components of the delivery catheter 78 have been retracted from the patient's vasculature, including the hollow guidewires 80, 82. The guidewires 90, 92 can remain in position in the renal arteries. As illustrated in FIG. 17, the first, smaller opening 64 of the endoluminal prosthesis 60 can be approximately aligned with the right renal artery 98. As mentioned, the first opening 64 can approximately match the size of the opening into the right renal artery 98. Additionally, with reference to FIG. 17, the second, larger opening 66 of the endoluminal prosthesis 60 can be positioned so that the main body 62 of the endoluminal prosthesis 60 does not cover or inhibit the flow of blood from the aortic artery 94 into the left renal artery 96.

Figure 18:
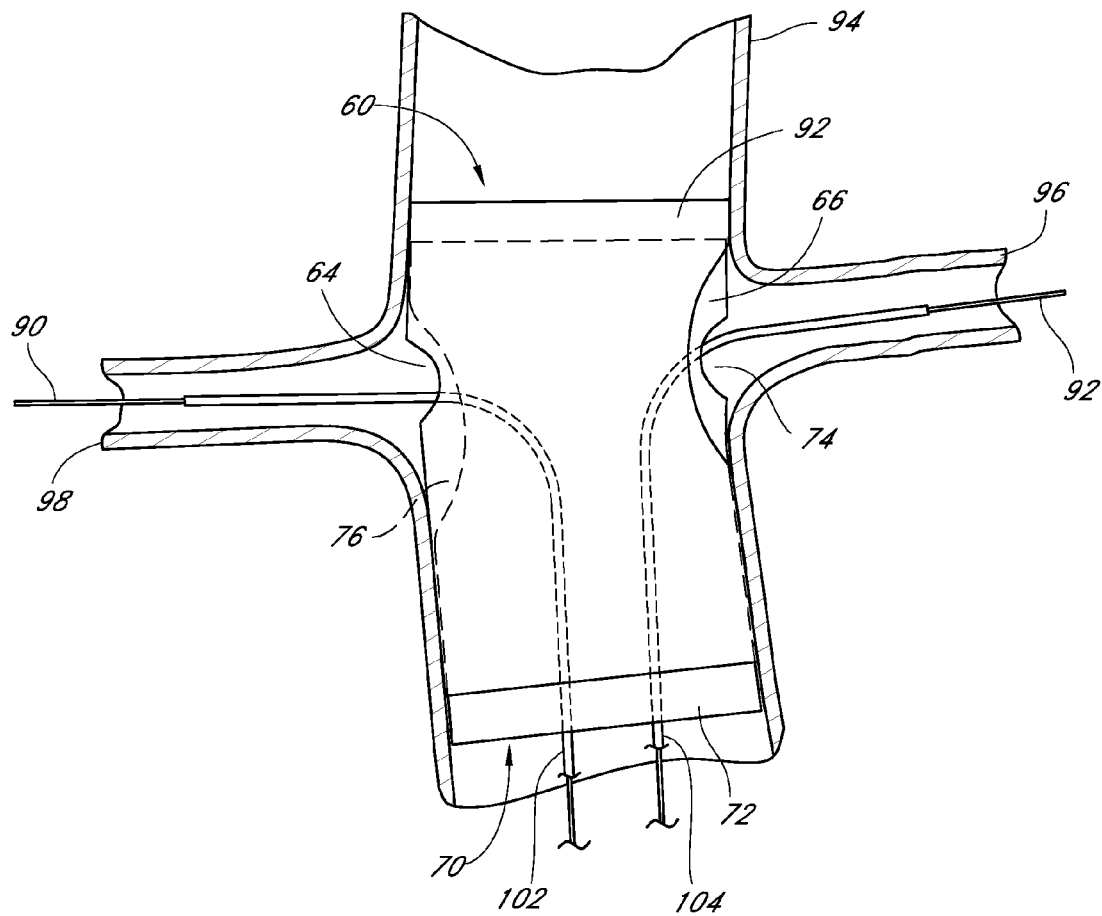
FIG. 18 is a partial section view of a patient's vasculature illustrating the endoluminal prosthesis illustrated in FIGS. 11A, 11B also deployed in the desired position within the patient's vasculature, after the components of the delivery system except for the guidewires have been retracted from the patient's vasculature.

FIG. 18 is a partial section view of a patient's vasculature illustrating the endoluminal prosthesis 70 illustrated in FIGS. 11A, 11B also deployed in the desired position within the patient's vasculature, after the components of the delivery system except for the guidewires have been retracted from the patient's vasculature. In FIG. 18, a second endoluminal prosthesis 70 has been positioned in the desired location in a similar fashion as has been described above with respect to the first endoluminal prosthesis 60. Again the hollow guidewires 102, 104 of the second delivery system can pass over the guidewires 90, 92, respectively. The opening 74 (which, again, can be relatively small as compared to opening 76) in the second endoluminal prosthesis 70 can be placed adjacent to the left renal artery 96. The opening 76 (which can be relatively large as compared to the first opening 74) in the second endoluminal prosthesis 70 can be placed adjacent to the right renal artery 98.

Figure 19:
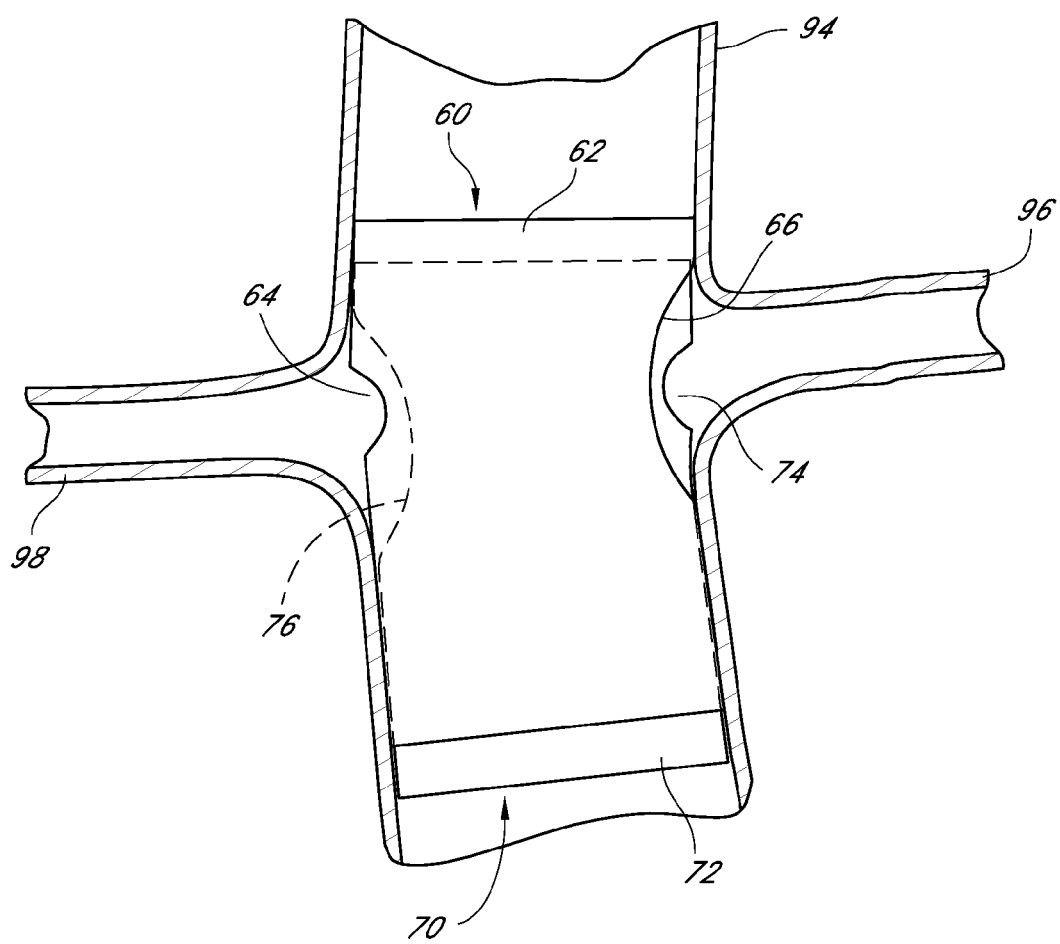
FIG. 19 is a partial section view of a patient's vasculature illustrating both endoluminal prostheses positioned in the desired position within the patient's vasculature, after the components of the delivery system have been retracted from the patient's vasculature.

FIG. 19 is a partial section view of a patient's vasculature illustrating both endoluminal prostheses 60, 70 positioned in the desired position within the patient's vasculature, after the components of the delivery system or systems have been retracted from the patient's vasculature. The small openings 64, 74 of the respective endoluminal prostheses 60, 70 provide fenestration to both renal arteries 98, 96, respectively. The overlapping endoluminal prostheses 60, 70 ensure a seal of the graft against the aorta. Thereafter, an expandable stent can be positioned and expanded within the endoluminal prostheses 60, 70, in a manner that is similar to the expandable stents described above, or in any suitable manner. While the prostheses 60, 70 are described as being self-expandable, in modified embodiments, one or both of the prostheses 60, 70 can be partially or wholly balloon expandable, or expandable by any other means.

Figure 20:
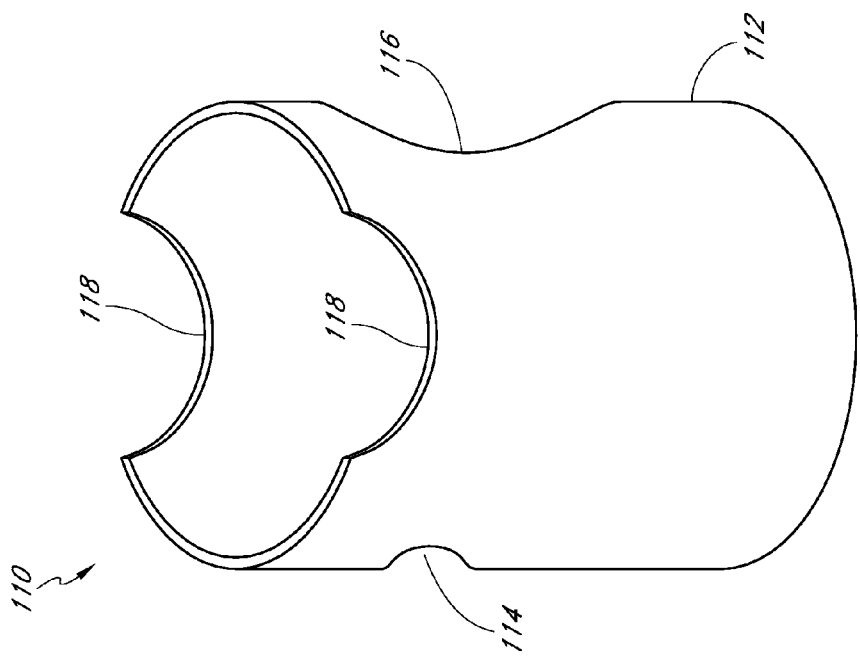
FIG. 20 is a perspective view of another embodiment of an endoluminal prosthesis with a scalloped end portion.

FIG. 20 is a perspective view of another embodiment of a fenestrated graft or endoluminal prosthesis 110 with a scalloped end portion. With reference to FIG. 20, the endoluminal prosthesis 110 can have a main body 112, a first, smaller opening 114, a second, larger opening 116, and one or more cutouts 118 (two being shown) formed at any desired location in an end portion of the main body 112 or at any location in the main body 112. In some embodiments, with the exception of the differences discussed herein and/or illustrated in FIG. 20, other aspects of the endoluminal prosthesis 110 can be the same as or similar to any of the other endoluminal prostheses disclosed herein, including but not limited to the endoluminal prostheses 10, 60 disclosed herein. Furthermore, the endoluminal prosthesis 110 can be deployed and secured in the desired vascular location by any of the same methods as described above with respect to any other endoluminal prostheses, including but not limited to the endoluminal prostheses 10, 60. The one or more cutouts 118 can be sized and position so that the main body 112 of the endoluminal prosthesis 110 does not significantly obstruct the flow into any other branch arteries.

For example, the cutouts 118 can be advantageous when positioning the endoluminal prosthesis 110 in the vasculature below the SMA. Any of the endoluminal prostheses or other grafts disclosed in this application or incorporated by reference herein can be formed so as to comprise the one or more cutouts 118 illustrated in FIG. 20. Again, in some embodiments, sutures or markers made from an RO material can be sewn into or attached to the endoluminal prosthesis 110 or any other prosthesis disclosed herein adjacent to one or more of the cutouts 118, one or more of the openings 114, 116 formed therein, near either of the end portions of the main body 112, or at any other suitable location.

Figure 21:
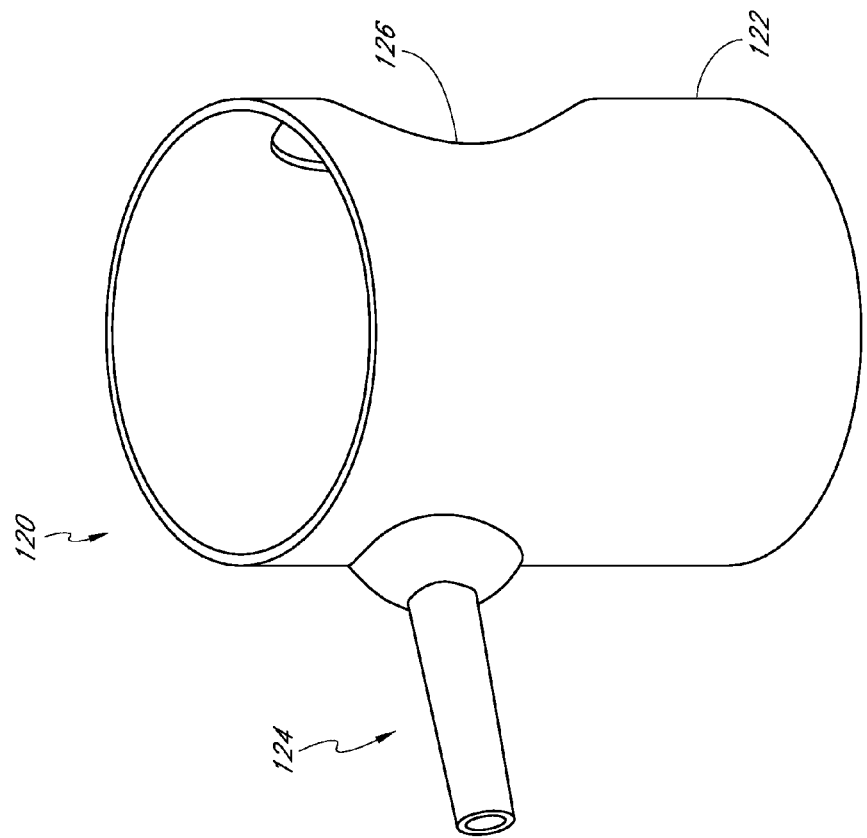
FIG. 21 is a perspective view of another embodiment of an endoluminal prosthesis with a large opening open to the proximal end of the graft.

FIG. 21 is a perspective view of another embodiment of an endoluminal prosthesis 120. In some embodiments, certain aspects of the endoluminal prosthesis 120 can be the same as or similar to any of the other endoluminal prostheses disclosed herein, including but not limited to the endoluminal prostheses 10, 60, 110 disclosed herein. Similar to the prosthesis 10 illustrated in FIG. 1A, the endoluminal prosthesis 120 can have a main body 122 and a branch graft 124. Additionally, similar to the prosthesis 60 disclosed herein, the endoluminal prosthesis 120 can have a larger opening 126 formed in the main body 122 at any desired axial or radial position. In some embodiments, the larger opening 126 can be positioned on the main body 122 at a radial position that opposes the branch graft 124 such that the axial centerline of the larger opening 126 is approximately parallel to the axial centerline of the branch graft 124.

In some embodiments, the branch graft 124 can be integrally formed with or can be sutured, adhered, or otherwise attached to the main body 122 in place of the first, smaller opening 64 described above with reference to endoluminal prosthesis 60. Accordingly, in some embodiments, the endoluminal prosthesis 120 can be deployed in the same manner as or similar to the method described above for deploying the endoluminal prosthesis 60. Alternatively, the endoluminal prosthesis 120 can be deployed by any suitable method. Similar to the embodiment of the endoluminal prosthesis 110 illustrated in FIG. 20, the endoluminal prosthesis 21 can also have one or more cutouts 118 (not shown) formed at any desired location in an end portion of the main body 122. Further, as with any other endoluminal prosthesis disclosed herein, in some embodiments, sutures or markers made from an RO material can be sewn into or attached to the endoluminal prosthesis 120 adjacent to one or more of the cutouts 118 (not illustrated), adjacent to the opening 126 formed in the main body 122, adjacent to or on the branch graft 124, near either of the end portions of the main body 112, and/or at any other suitable location.

Figure 22:
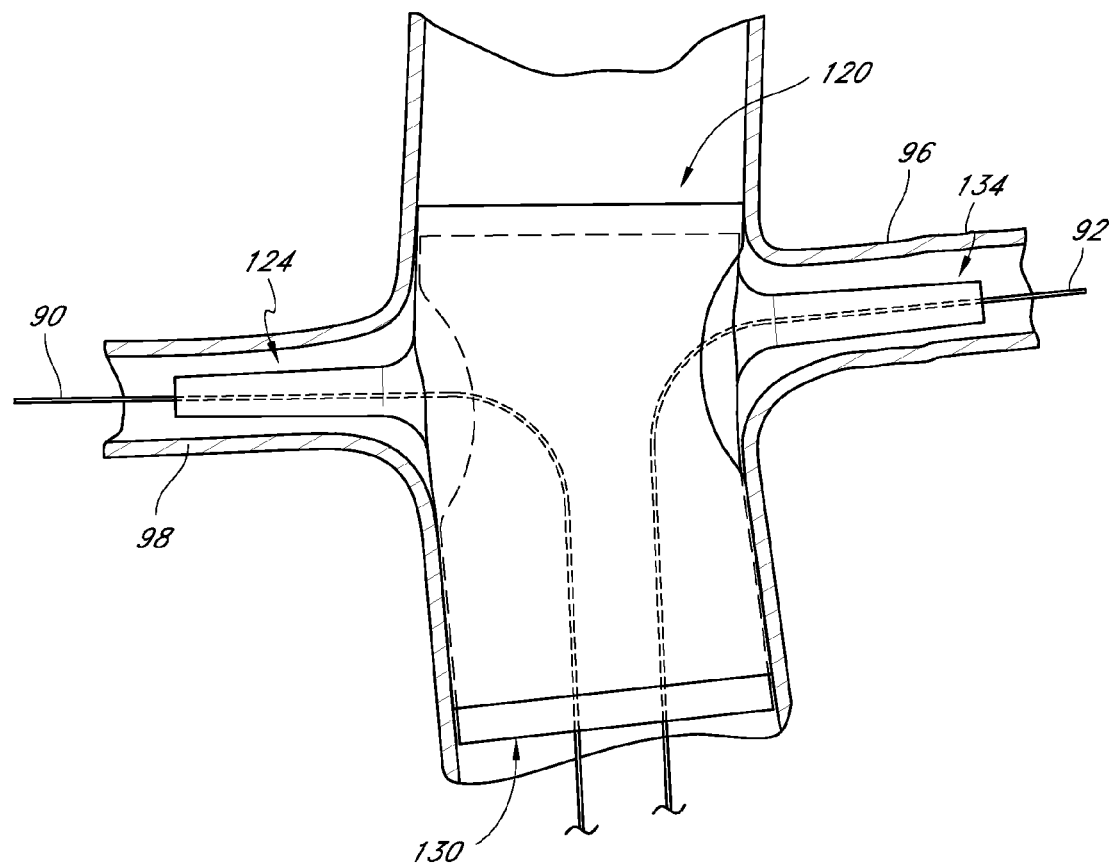
FIG. 22 is a partial section view of a patient's vasculature illustrating two of the endoluminal prostheses illustrated in FIG. 21 deployed in the desired position within the patient's vasculature, after the components of the delivery system except for the hollow guidewires have been retracted from the patient's vasculature.

With reference to FIGS. 22-27, a method of deploying the endoluminal prosthesis 120 will now be described. FIG. 22 is a partial section view of a patient's vasculature after a first and second endoluminal prosthesis 120, 130 have been positioned within the patient's vasculature, after the components of the delivery system except for the hollow guidewires 80, 82 have been retracted from the patient's vasculature. In some embodiments, as illustrated in FIG. 22, the second endoluminal prosthesis 130 can be the same as the first endoluminal prosthesis 120 described above. Further, with reference to FIG. 22, the branch graft 124 of the first endoluminal prosthesis 120 can be positioned in the right renal artery 98, while the branch graft 134 of the second endoluminal prosthesis 130 can be positioned within the left renal artery 96.

Similar to the fenestrated endoluminal prostheses described above, each endoluminal prosthesis 120, 130 is independently positionable so as to accommodate a wide range of vasculature geometries or renal arteries without requiring a medical practitioner to custom make the endoluminal prosthesis. In some embodiments, the branch graft 124, 134 in the endoluminal prostheses 120, 130 can be sized to match the renal artery or branch vessel that the branch graft 124, 134 is intended to be inserted into. The position and size of the second larger opening can be configured such that it accommodates a wide range of branch vessel configurations.

Figure 23:
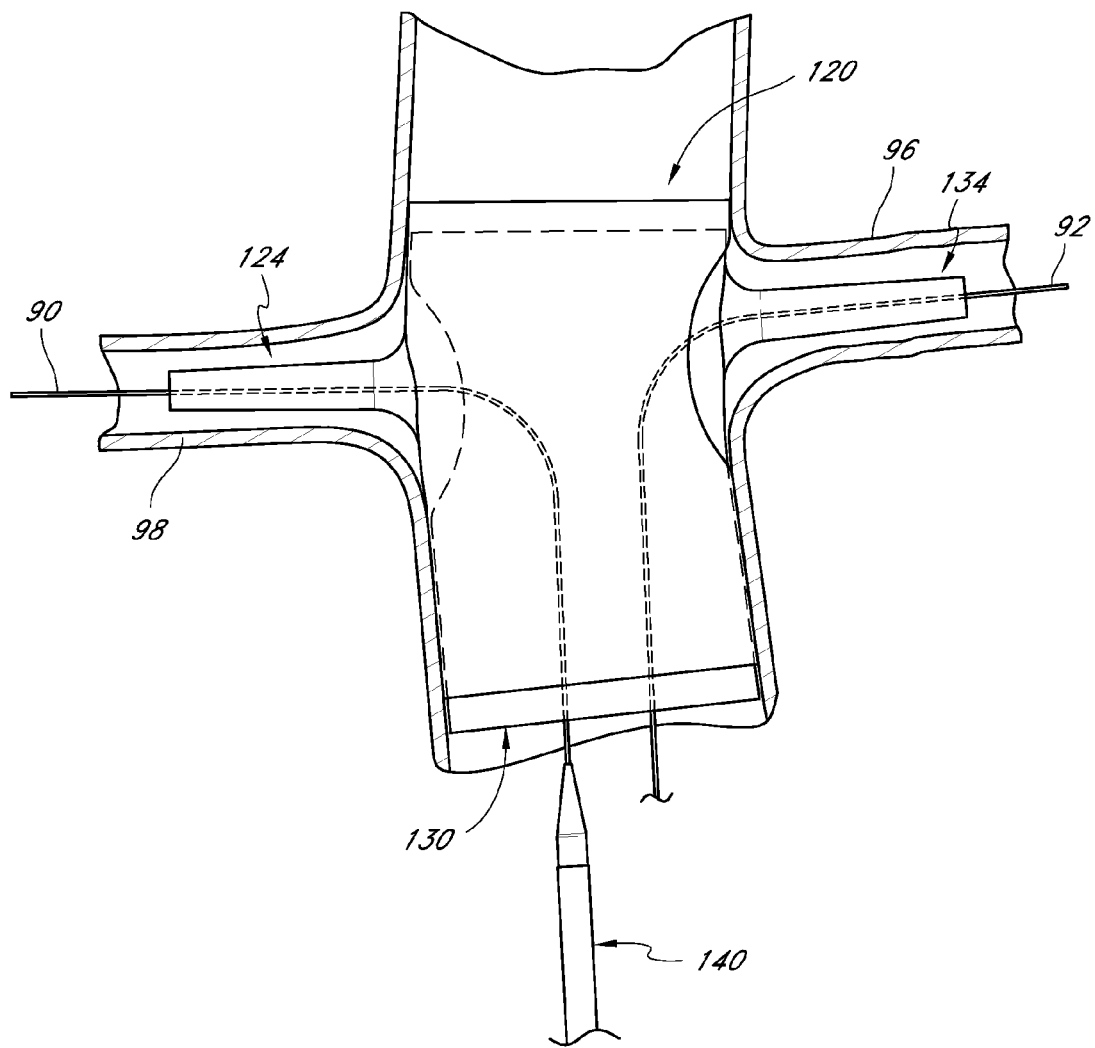
FIGS. 23 and 24 are partial section views of a patient's vasculature illustrating two of the endoluminal prostheses illustrated in FIG. 21 deployed in the desired position within the patient's vasculature, further illustrating a branch graft deployment catheter being guided into the right renal artery over a guidewire.
Figure 24:
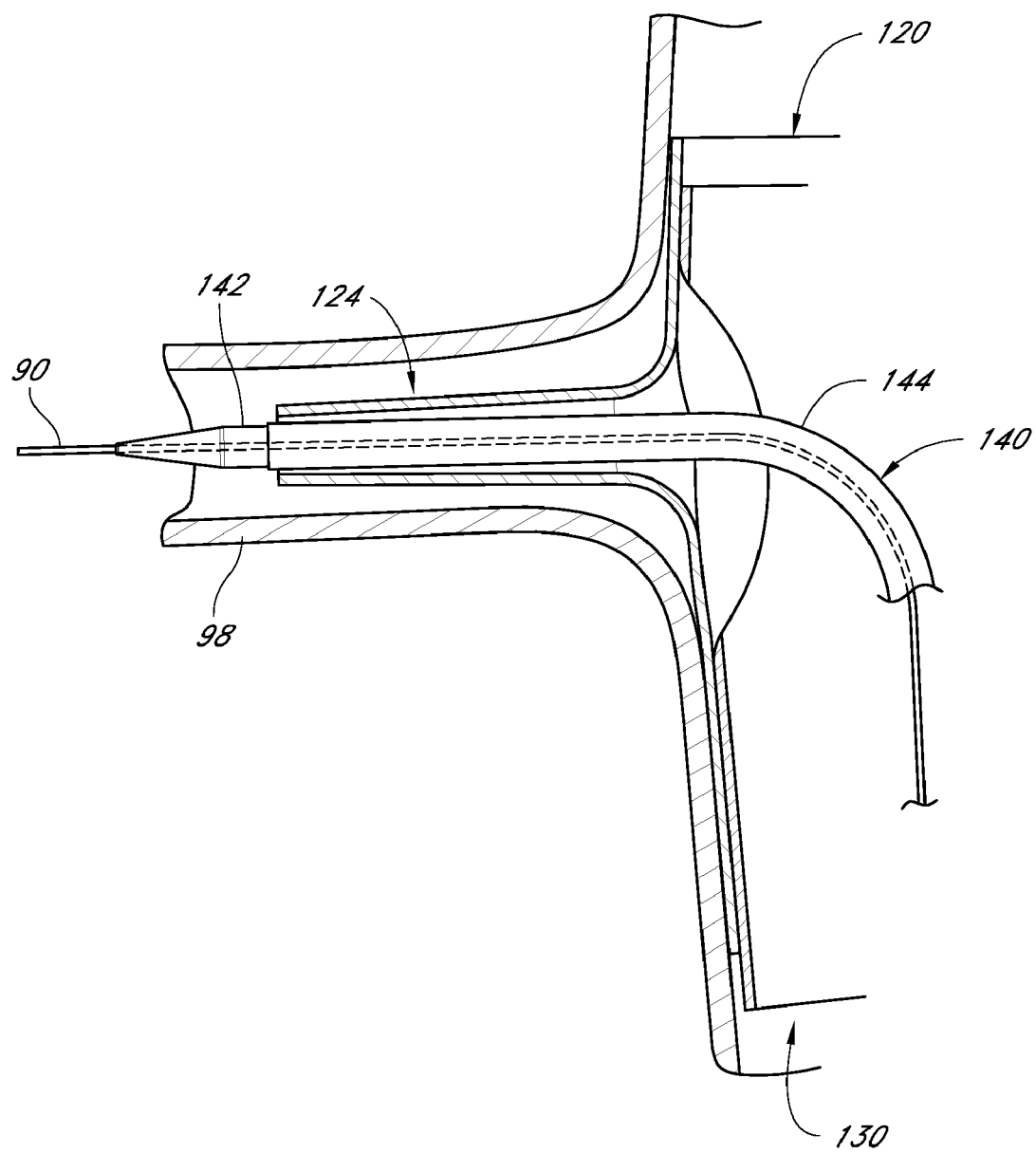

Similar to the deployment of the endoluminal prostheses 60, 70 described above, the guidewires 90, 92 can be used for positioning each of the endoluminal prostheses 120, 130, and for guiding the delivery catheter for each of the branch stents, as will be described below. FIGS. 23 and 24 are partial section views of a patient's vasculature illustrating the endoluminal prostheses 120, 130 deployed in the desired position within the patient's vasculature, further illustrating a branch graft deployment catheter 140 being guided into the right renal artery 98 over the guidewire 90. With reference to FIGS. 23 and 24, after the first and second endoluminal prostheses 120, 130 have been positioned in the desired location in the patient's vasculature, the branch graft deployment catheter 140 can be guided up the guide wire 90 into the right renal artery 98. Optionally, if the branch graft deployment catheter has a balloon supported by the distal end thereof, the balloon can be inflated to secure the branch graft deployment catheter within the renal artery, as discussed above. Additionally, in some embodiments, coils or hooks supported by the distal end of the branch graft deployment catheter can be used to secure the branch graft deployment catheter within the renal artery.

Figure 25:
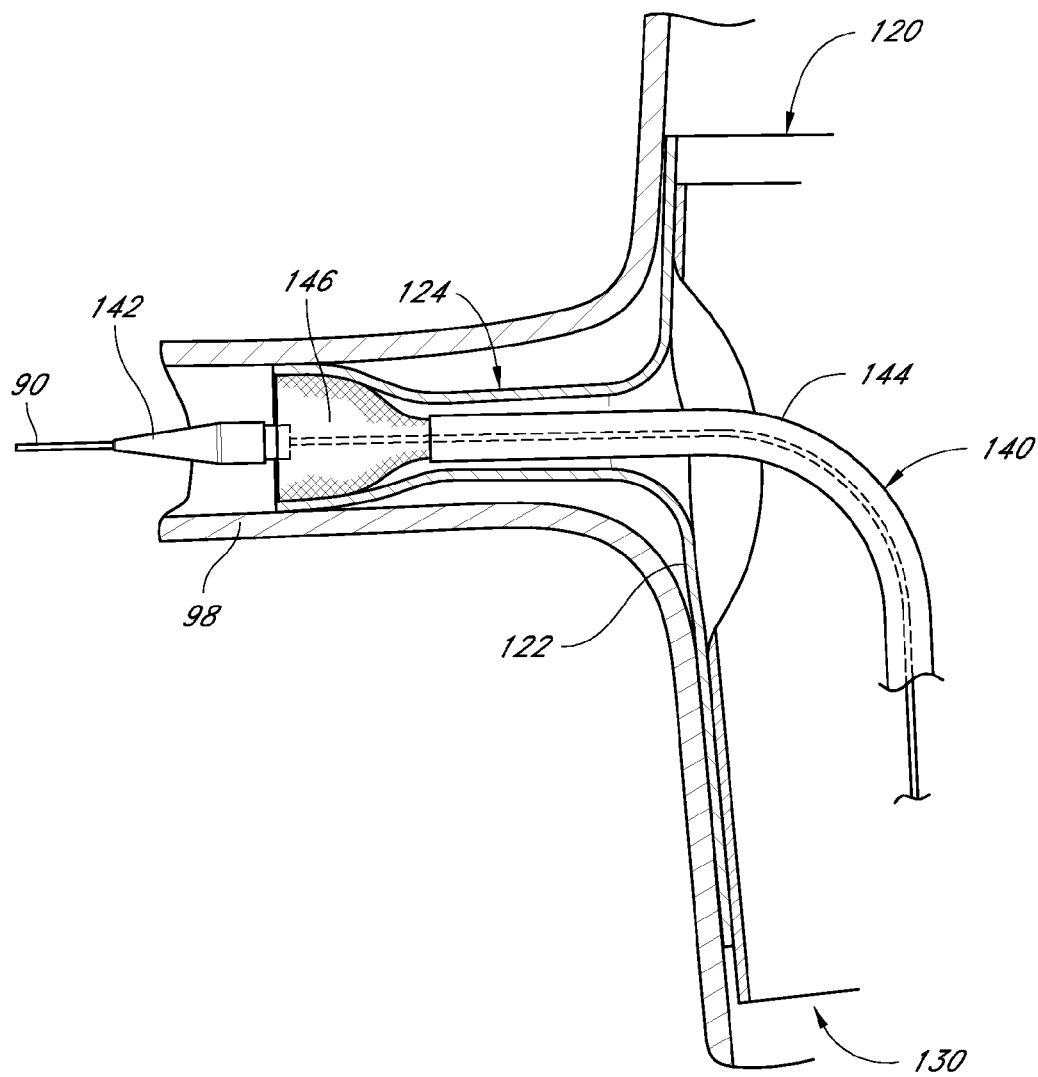
FIG. 25 is a partial section view of a patient's vasculature illustrating an embodiment of a stent being deployed in the branch graft positioned in a patient's right renal artery.

Once the deployment catheter 140 has reached the desired position such that the catheter tip 142 has extended past the end of the branch graft 124, as illustrated in FIG. 24, the outer sheath 144 of the deployment catheter 140 can be retracted to deploy the stent 146 supported within the deployment catheter 140, as illustrated in FIG. 25. The stent 146 illustrated in FIG. 24 is a self expanding stent. However, the procedures disclosed herein can easily be modified to accommodate a balloon expandable or other stent suitable for such use.

Figure 26:
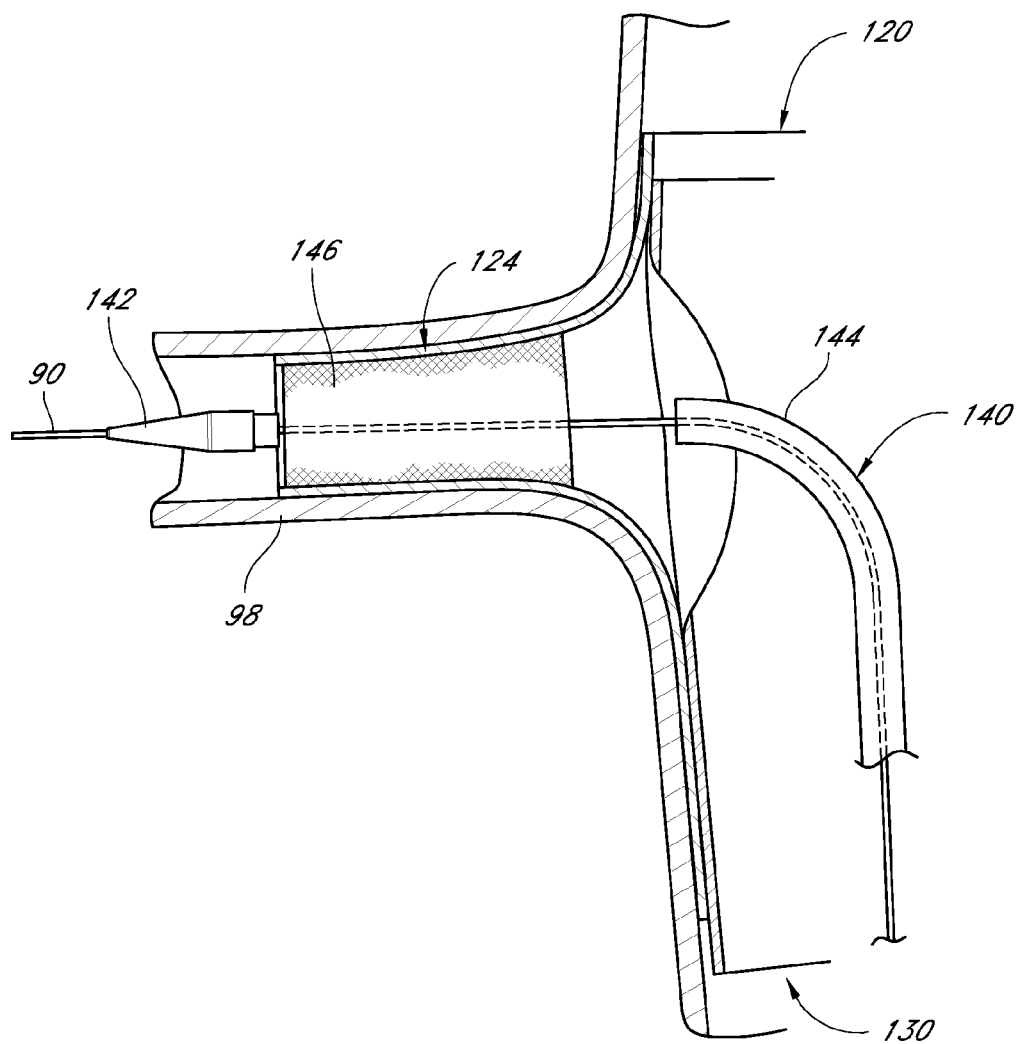
FIG. 26 is a partial section view of a patient's vasculature illustrating an embodiment of a stent after it has been deployed in the branch graft positioned in a patient's right renal artery.

As mentioned above, FIG. 25 is a partial section view of a patient's vasculature illustrating an embodiment of a stent 146 being deployed in the branch graft 124 positioned in a patient's right renal artery 98 by proximally retracting the outer sheath 144 of the deployment catheter 140. FIG. 26 illustrates the patient's vasculature after the stent 142 has been completely deployed in the branch graft 124 positioned in a patient's right renal artery 98. As illustrated therein, the expansion of the stent 146 can cause the branch graft 124 to expand against the blood vessel 98, so as to secure the graft 124 in the desired position. Note that, in some embodiments, the proximal portion of the branch graft 124 (i.e. a portion of the branch graft 124 closest to the main body 122 of the endoluminal prosthesis 120, as illustrated in FIG. 25) can be pre-expanded to more approximately match the patient's vasculature in the pre-deployed state, as was described above with reference to endoluminal prosthesis 10.

Figure 27:
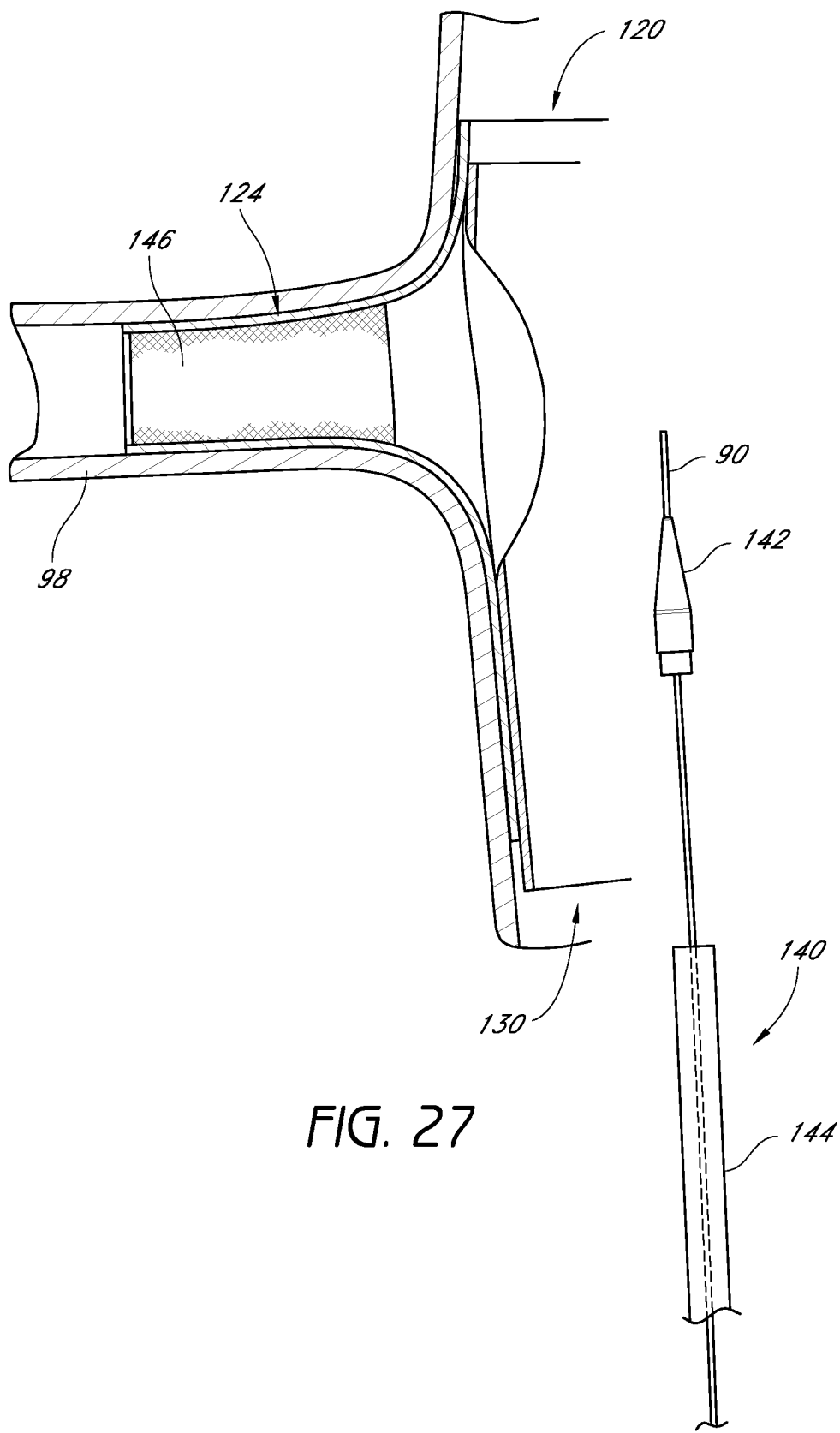
FIG. 27 is a partial section view of a patient's vasculature illustrating an embodiment of a stent after it has been deployed in the branch graft positioned in a patient's right renal artery, further illustrating the delivery catheter being removed from the patient's vasculature.

Finally, FIG. 27 is a partial section view of a patient's vasculature illustrating an embodiment of a stent 142 after it has been completely deployed in the branch graft 124 positioned in a patient's right renal artery 98, further illustrating the delivery catheter 140 being removed from the patient's vasculature. Following the procedures described in connection with FIGS. 22-27, a stent similar to the stent 146 described above can be deployed in the branch graft 134 of the second endoluminal prosthesis 130, so that the branch graft 134 in the left renal artery 96 can be supported in the desired position.

Alternatively, the branch grafts 124, 134 can be expanded within the renal artery in a manner similar to any of the methods disclosed herein for expanding the branch graft 14 in the blood vessel or renal artery. Alternatively, the branch grafts 124, 134 can be expanded within the blood vessel or renal artery following any other suitable method, which can include deploying a self-expanding or balloon expandable bare metal stent or graft covered stent therein after the branch grafts 124, 134 have been positioned in the desired blood vessel or renal artery.

Additionally, any of the endoluminal prostheses described herein can be used independently or can be used in conjunction one or more additional grafts, including the grafts disclosed herein or any other suitable grafts such as other tubular or bifurcated grafts. For example, without limitation, any of the endoluminal prostheses disclosed herein or incorporated herein by reference, or either or both of the endoluminal prostheses 120, 130 can be used in conjunction with an additional prosthesis configured the same as or similar to the endoluminal prosthesis 120 to accommodate additional branch vessels, and/or any other suitable prostheses, such as without limitation a bifurcated prosthesis.

Additionally, without limitation, any of the endoluminal prostheses disclosed herein or incorporated herein by reference, or either or both of the endoluminal prostheses 120, 130 can be used with any bifurcated graft positioned in a patient's vasculature to protect a patient's AAA. In this application, one or more of the endoluminal prostheses disclosed herein (including but not limited to endoluminal prostheses 10, 30, 40, 50, 60, 70, 110, and/or 120) can be deployed within the patient's vasculature after the bifurcated graft has been deployed across the patient's AAA. In this manner, the endoluminal prostheses disclosed herein will be positioned within the bifurcated graft it has been deployed across the patient's AAA so as to minimize or prevent blood from flowing between the main tubular portion of the bifurcated graft and the patient's blood vessel.

One of ordinary skill in the art will recognize many configurations of the fenestrated grafts described herein for the treatment of a main vessel having two or more branch vessels. As described herein, in some embodiments, the overlap of two or more portions of the endoluminal prostheses each having at least one small and one large opening can combine to create an endoluminal prosthesis system with two or more small openings, which can be used address a wide range of vasculature geometries without requiring any custom fabrication of the prostheses.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and subcombinations are intended to fall within the scope of this disclosure.

As will be recognized, certain embodiments described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

For example, while some embodiments of the delivery and graft systems are described herein with respect to the abdominal aortic artery, the delivery and graft systems can be used for repairing vasculature in other portions of the body, including but not limited to the SMA, the inferior mesenteric artery, or any other arteries or blood vessels in the body suitable for such procedures or apparatuses.

What is claimed is:

1. An endoluminal prosthesis system comprising:
a first endoluminal prosthesis comprising a first main graft body comprising a first axial opening, a second axial opening, a first lumen extending between the first and second axial openings of the first main graft body, a first lateral opening formed laterally through the first main graft body and in communication with the first lumen, and a second lateral opening formed laterally through the first main graft body and in communication with the first lumen;
a second endoluminal prosthesis comprising a second main graft body comprising a first axial opening, a second axial opening, a first lumen extending between the first and second axial openings of the second main graft body, a first lateral opening formed laterally through the first main graft body and in communication with the first lumen, and a second lateral opening formed laterally through the first main graft body and in communication with the first lumen; and
a hollow guidewire advanced through at least a portion of the first lumen of the first main graft body and through one of the first and second lateral openings of the first main graft body when the first main graft body is in a collapsed, pre-delivery state;
wherein:
the first lateral opening in the first main graft body is smaller than the second lateral opening in the first main graft body;
the first lateral opening in the second main graft body is smaller than the second lateral opening in the second main graft body;
the second main graft body is configured to be expandable substantially within the first main graft body such that the second lateral opening of the second main graft body does not cover any portion of the first lateral opening in the first main graft body, and such that the second lateral opening of the first main graft body does not cover any portion of the first lateral opening in the second main graft body; and
when the second main graft body has been expanded within the first main graft body, the resulting endoluminal prosthesis system has two lateral openings therein that are each approximately equivalent in size to the first lateral opening in each of the first and second main graft bodies.

2. The endoluminal prosthesis system of claim 1, wherein the main graft body of each of the first and second endoluminal prostheses defines a generally tubular shape.

3. The endoluminal prosthesis system of claim 1, wherein the first lateral opening in at least one of the first and second main graft bodies is approximately diametrically opposed to the second lateral opening in the same main graft body.

4. The endoluminal prosthesis system of claim 1, wherein the first lateral opening in each of the first and second main graft bodies is approximately one-half the size of the second lateral opening in each of the first and second main graft bodies.

5. The endoluminal prosthesis system of claim 1, wherein the second lateral opening in each of the first and second main graft bodies defines a diameter that is at least approximately three times greater than the diameter of the first lateral opening in each of the first and second main graft bodies.

6. The endoluminal prosthesis system of claim 1, wherein the second lateral opening in each of the first and second main graft bodies defines a diameter that is at least approximately four times greater than the diameter of the first lateral opening in each of the first and second main graft bodies.

7. The endoluminal prosthesis system of claim 1, wherein the two small lateral openings in the resulting endoluminal prosthesis system are not mutually opposing.

8. The endoluminal prosthesis system of claim 1, wherein at least one of the first and second main graft bodies comprises one or more cutouts in an end portion thereof.

9. The endoluminal prosthesis system of claim 1, wherein the first lateral opening in the first main graft body comprises a branch graft attached to the first main graft body so as to surround the first lateral opening in the first main graft body.

10. The endoluminal prosthesis system of claim 9, wherein the branch graft attached to the first main graft body is expandable with a bare or covered metal stent.

11. The endoluminal prosthesis system of claim 9, wherein the first lateral opening in the second main graft body comprises a branch graft attached to the second main graft body so as to surround the first lateral opening in the second main graft body.

12. The endoluminal prosthesis system of claim 11, wherein at least one of the branch graft attached to the first main graft body and the branch graft attached to the second main graft body is expandable with a bare or covered metal stent.

13. The endoluminal prosthesis system of claim 1, further comprising a third endoluminal prosthesis positioned adjacent to or overlapping with at least a portion of one of the first endoluminal prosthesis and the second endoluminal prosthesis.

14. The endoluminal prosthesis system of claim 13, wherein the third prosthesis is a bifurcated endoluminal prosthesis.

15. The endoluminal prosthesis system of claim 13, wherein the third prosthesis is a bifurcated endoluminal prosthesis configured to be positioned adjacent to an abdominal aortic aneurysm.

16. The endoluminal prosthesis system of claim 13, wherein the third prosthesis comprises a third main graft body having at least a first and a second lateral opening therein, wherein the third main graft body is configured such that at least a portion of the third main body is expandable within the second main graft body.

17. The endoluminal prosthesis system of claim 1, wherein at least one of the first endoluminal prosthesis and the second endoluminal prosthesis comprises a distensible polymeric material.

18. The endoluminal prosthesis system of claim 17, wherein the polymeric material is selected from the group consisting of PTFE, ePTFE, Dacron, Dacron®, Teflon®, and polyester.

19. The endoluminal prosthesis system of claim 1, wherein at least one of the first endoluminal prosthesis and the second endoluminal prosthesis has at least one radiopaque suture or marker attached thereto.

20. An endoluminal prosthesis comprising:
a first main graft body comprising a first axial opening, a second axial opening, a first lumen extending between the first and second axial openings of the first main graft body, a first lateral opening formed laterally through the first main graft body and in communication with the first lumen, and a second lateral opening formed laterally through the first main graft body and in communication with the first lumen thereof;
a first branch graft having a proximal end portion, a distal end portion, and an axial opening therethrough, the first branch graft being supported by the first main graft body so that the proximal end portion of the first branch graft is positioned adjacent to the first lateral opening in the first main graft body and so that the axial opening through first branch graft is in communication with the first lateral opening formed in the first main graft body; and a second main graft body comprising a first axial opening, a second axial opening, a first lumen extending between the first and second axial openings of the second main graft body, a first lateral opening formed laterally through the first main graft body and in communication with the first lumen, and a second lateral opening formed laterally through the second main graft body and in communication with the first lumen thereof;

wherein:
- the first lateral opening in the first main graft body is smaller than the second lateral opening in the first main graft body;
- the first lateral opening in the second main graft body is smaller than the second lateral opening in the second main graft body;
- the second main graft body is configured to be expandable substantially within the first main graft body such that the second lateral opening of the second main graft body does not cover any portion of the first lateral opening in the first main graft body or the first branch graft, and such that the second lateral opening of the first main graft body does not cover any portion of the first lateral opening in the second main graft body; and
- when the second main graft body has been expanded within the first main graft body, the resulting endoluminal prosthesis system has two lateral openings therein that are each approximately equivalent in size to the first lateral opening in each of the first and second main graft bodies, the first lateral opening of the first main graft body having the first branch graft supported adjacent thereto.

21. The endoluminal prosthesis of claim 20, wherein a diameter of the distal end portion of the first branch graft is smaller than a diameter of the proximal end portion of the first branch graft when the first branch graft is in an unexpanded state, and wherein the distal end portion of the first branch graft is expandable in a branch blood vessel to a diameter that is approximately equal to the diameter of the proximal end portion of the first branch graft.

22. The endoluminal prosthesis of claim 21, wherein the distal end portion of the branch graft is expandable in a branch blood vessel using a balloon expander.

23. The endoluminal prosthesis of claim 20, further comprising a second branch graft supported by the second main graft body so that a proximal end portion of the second branch graft is positioned adjacent to the first lateral opening in the second main graft body and so that an axial opening through second branch graft is in communication with the first lateral opening formed in the second main graft body.

24. The endoluminal prosthesis of claim 20, further comprising a hollow guidewire advanced through at least a portion of the first lumen of the first main graft body and through the first lateral opening of the first main graft body when the first main graft body is in a collapsed, pre-delivery state.

* * * * *